United States Patent
Wu et al.

(10) Patent No.: US 11,013,582 B2
(45) Date of Patent: *May 25, 2021

(54) THREE-DIMENSIONAL TOOTH MODELING USING A TWO-DIMENSIONAL X-RAY IMAGE

(71) Applicant: Align Technology, Inc., San Jose, CA (US)

(72) Inventors: Fuming Wu, Pleasanton, CA (US); Vadim Matov, San Jose, CA (US); Jihua Cheng, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 459 days.

This patent is subject to a terminal disclaimer.

(21) Appl. No.: 16/113,018

(22) Filed: Aug. 27, 2018

(65) Prior Publication Data

US 2019/0029783 A1 Jan. 31, 2019

Related U.S. Application Data

(63) Continuation of application No. 14/622,763, filed on Feb. 13, 2015, now Pat. No. 10,076,389.

(51) Int. Cl.
*A61C 13/00* (2006.01)
*G16Z 99/00* (2019.01)
(Continued)

(52) U.S. Cl.
CPC .......... *A61C 13/0004* (2013.01); *A61C 7/002* (2013.01); *G16Z 99/00* (2019.02); *A61C 2007/004* (2013.01); *G06F 30/00* (2020.01)

(58) Field of Classification Search
CPC .............. A61C 13/0004; A61C 7/002; A61C 2007/004; G16Z 99/00; G06F 30/00; G16H 50/50
See application file for complete search history.

(56) References Cited

U.S. PATENT DOCUMENTS 7,080,979 B2 * 7/2006 Rubbert ............... A61C 9/0053
433/24
7,156,655 B2  1/2007 Sachdeva et al.
(Continued)

FOREIGN PATENT DOCUMENTS

JP  2011-039869 A  2/2011
KR  10-1397476 B1  5/2014

OTHER PUBLICATIONS

Sridhar, B. "Finding 3D Teeth Positing by using 2D Uncalibrated Dental X-Ray images" Thesis, Blekinge Institute of Technology (2010).
(Continued)

*Primary Examiner* — Jay Hann
(74) *Attorney, Agent, or Firm* — Lowenstein Sandler LLP

(57) ABSTRACT

A method and system generate a scan model that is a mathematical model to simulate an imaging process performed by an x-ray imaging device that created a two-dimensional x-ray image of at least one tooth. The scan model uses an initial estimate of one or more parameters of the x-ray imaging device to simulate the imaging process on a three-dimensional model. The method and system generate the two-dimensional contour of the three-dimensional model based on the scan model that uses the initial estimate of the one or more parameters of the x-ray imaging device. The method and system adjust the two-dimensional contour to cause a first component of the two-dimensional contour to approximately align with a second component of the two-dimensional x-ray image. The method and system calibrate the scan model based on data obtained from adjusting the two-dimensional contour.

20 Claims, 15 Drawing Sheets

(51) Int. Cl.
    *A61C 7/00*     (2006.01)
    *G06F 30/00*     (2020.01)

(56) References Cited

U.S. PATENT DOCUMENTS

| | | |
|---|---|---|
| 7,234,937 B2 | 6/2007 | Sachdeva et al. |
| 7,245,753 B2 | 7/2007 | Squilla et al. |
| 7,844,429 B2 | 11/2010 | Matov et al. |
| 7,865,259 B2 | 1/2011 | Kuo et al. |
| 8,135,569 B2 | 3/2012 | Matov et al. |
| 8,254,520 B2 | 8/2012 | Sadakane et al. |
| 2007/0134613 A1 | 6/2007 | Kuo et al. |
| 2009/0148809 A1 | 6/2009 | Kuo et al. |
| 2010/0167243 A1 | 7/2010 | Spiridonov et al. |
| 2012/0095732 A1 | 4/2012 | Fisker et al. |

OTHER PUBLICATIONS

Enciso et al., "3D Tooth Shape from Radiographs using Thin-Plates Splines," Craniofacial Virtual Realty Lab, DEN 312, Integrated Media System Center EEB 131, University of Souther California, 2003.

Mazzotta et al., "From 2D to 3D: Construction of a 3D Parametric Model for Detection of Dental Roots Shapes and Position from a Panoramic Radiograph—A Preliminary Report", International Journal of Dentistry, International Journal of Dentistry, vol. 2013(2013), Article ID 964631, 8 pages.

International Search Report and Written Opinion of the International Searching Authority for PCT Application PCT/IB2016/000138 dated May 2, 2016.

* cited by examiner

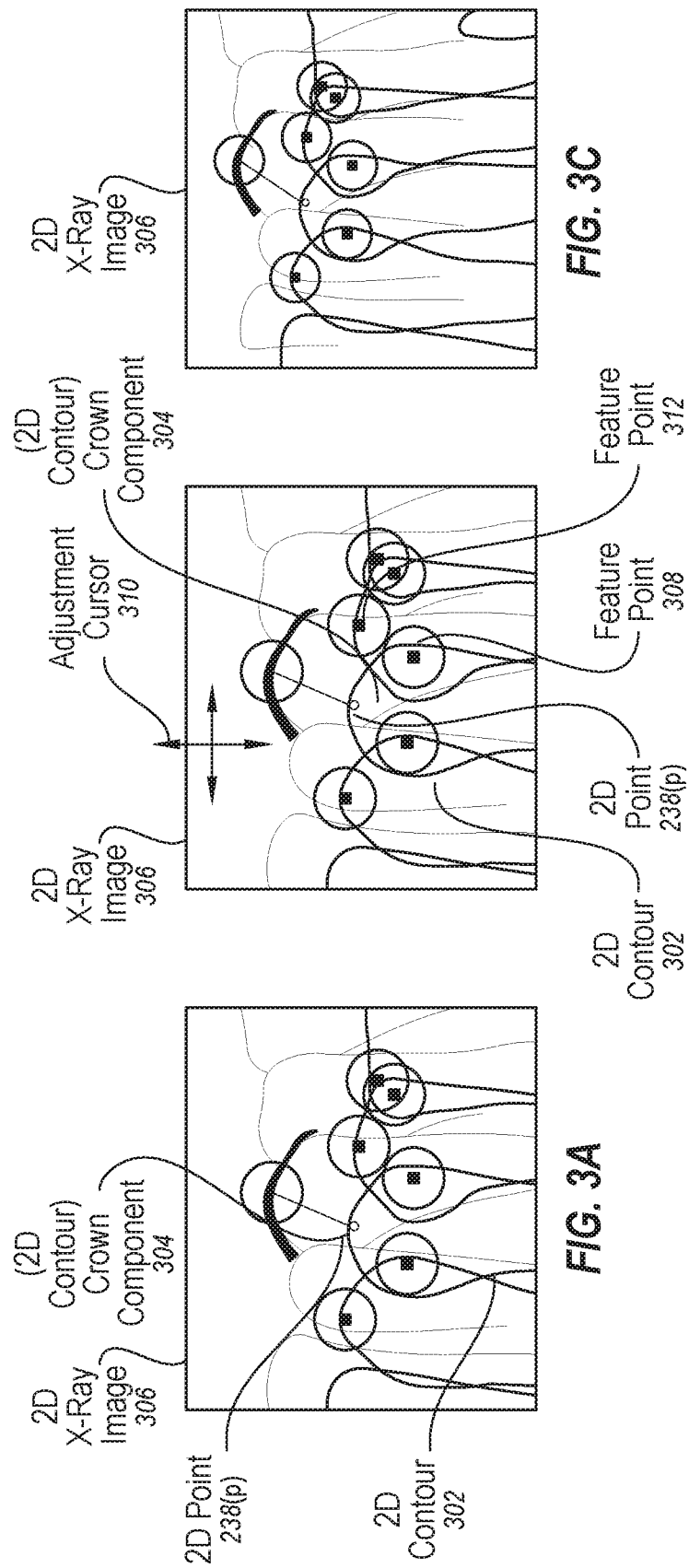

THREE-DIMENSIONAL TOOTH MODELING USING A TWO-DIMENSIONAL X-RAY IMAGE

RELATED APPLICATION

This application is a continuation application of U.S. patent application Ser. No. 14/622,763, filed Feb. 13, 2015, the entire contents of which are hereby incorporated by reference herein.

TECHNICAL FIELD

Embodiments of the present invention relate to the field of dental treatment and, in particular, to a system and method for three-dimensional modeling of at least one complete tooth using a two-dimensional x-ray image.

BACKGROUND

In prosthodontic procedures designed to implant a dental prosthesis in the oral cavity, the dental site at which the prosthesis is to be implanted may be measured accurately and studied carefully, so that a prosthesis such as a crown, denture or bridge, for example, can be properly designed and dimensioned to fit in place. A good fit, for example, enables mechanical stresses to be properly transmitted between the prosthesis and the jaw and minimizes infection of the gums via the interface between the prosthesis and the dental site.

Some procedures call for removable prosthetics to be fabricated to replace one or more missing teeth, such as a partial or full denture, in which case the surface contours of the areas where the teeth are missing may be reproduced accurately so that the resulting prosthetic fits over the edentulous region with even pressure on the soft tissues.

In some practices, the dental site is prepared by a dental practitioner, and a positive physical model of the dental site is constructed. Alternatively, the dental site may be scanned to provide three-dimensional (3D) data of the dental site. In either case, the virtual or real model of the dental site may be sent to a dental lab that manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry may need to be altered to avoid the collision. Further, if the area of the preparation containing a finish line lacks definition, it may not be possible to properly determine the finish line and thus the lower edge of the coping may not be properly designed. Indeed, in some circumstances, the model is rejected and the dental practitioner then re-scans the dental site, or reworks the preparation, so that a suitable prosthesis may be produced.

In orthodontic procedures, it can be important to provide a model of one or both dental arches and/or jaws. Where such orthodontic procedures are designed virtually, a virtual 3D model of the oral cavity is also beneficial. Such a virtual 3D model may be obtained by scanning the oral cavity directly, or by producing a physical model of the dentition, and then scanning the model with a suitable scanner.

Thus, in both prosthodontic and orthodontic procedures, obtaining a 3D model of a dental site in the oral cavity may be an initial procedure that is performed. When the 3D model is a virtual model, the more complete and accurate the scans of the dental site are, the higher the quality of the virtual model, and thus the greater the ability to design an optimal prosthesis or orthodontic treatment appliance.

BRIEF DESCRIPTION OF THE DRAWINGS

The present invention is illustrated by way of example, and not by way of limitation, in the figures of the accompanying drawings.

FIG. 3A illustrates a crown component of a two-dimensional contour overlaid on an x-ray image, in accordance with embodiments of the present invention.

FIG. 3B illustrates adjustment of a crown component of a two-dimensional contour of FIG. 3A, in accordance with embodiments of the present invention.

FIG. 3C illustrates calibration of a scan model based on data from adjusting the crown component of a two-dimensional contour of FIG. 3B, in accordance with embodiments of the present invention.

DETAILED DESCRIPTION

Figure 1:
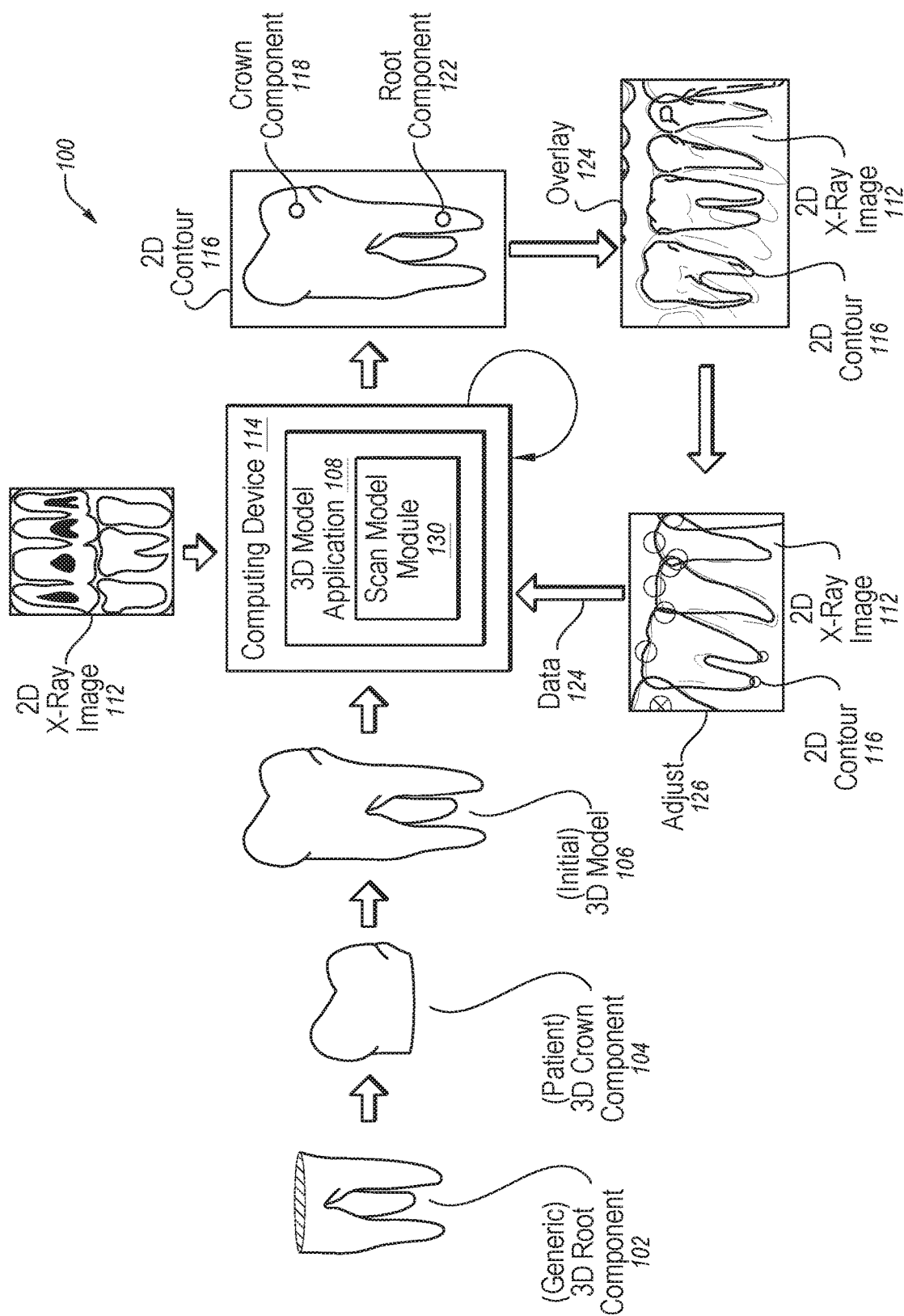
FIG. 1 illustrates an exemplary system for tooth modeling, in accordance with embodiments of the present invention.

Described herein is a method and apparatus for improving the quality of three-dimensional models, such as three-dimensional tooth models (e.g., virtual models) of dental sites for patients. High quality and accurate three-dimensional models of a dental site may provide improved orthodontic diagnoses and treatment, such as greater ability to design an optimal prosthesis or orthodontic treatment appliance. Three-dimensional modeling techniques may employ a variety of techniques, such as optical scanning techniques, that provide information of features of the dental site above the gum line. However, for optical scanning techniques information below the gum line, in particular geometry of tooth roots, may be incomplete or missing entirely. This may lead to inaccurate and/or clinically incorrect three-dimensional tooth models. Three-dimensional x-ray techniques may be used to gather information of the dental site below the gum line. However, such techniques may expose patients to a large amount of radiation and the x-ray equipment to perform three-dimensional x-ray image capture may be expensive, cumbersome, and bulky. Two-dimensional x-ray techniques, such as panoramic x-ray, may expose a patient to less radiation and two-dimensional x-ray devices may be less expensive and more commonly used among dental practitioners. Embodiments described herein provide a 3D tooth modeling system that uses both 3D optical scanning and 2D x-ray imaging to create a 3D tooth model that includes both accurate crown and root information.

In one embodiment, an initial three-dimensional (3D) tooth model of a patient may be received. The 3D tooth model may include a 3D crown component from a scan, such as an intraoral scan, of the patient. The 3D tooth model may alternatively be based on a 3D scan of a physical model generated from a mold of a patient's dental arch. The 3D tooth model may also include a generic 3D root component from a template. The 3D crown component and root component may be combined together to form an initial 3D tooth model. Additionally, a two-dimensional (2D) x-ray image, such as a panoramic x-ray image, may be received. An x-ray image device that creates the 2D x-ray images may have certain parameters such as a coordinate system parameter, a scan angle parameter, an arch length parameter, and/or an elliptical arch parameter. A scan model (e.g., a panoramic x-ray scan model) may be generated that includes an estimate of one or more of the parameters of the x-ray imaging device. The scan model may be used to project a 3D tooth model into a 2D contour, and vice versa. After the initial 3D tooth model is projected as a 2D contour using the scan model, the 2D contour may be overlaid on the 2D x-ray image. The 2D contour may be adjusted to align with the 2D x-ray image. In particular, the 2D crown component of the 2D contour may be aligned with the corresponding crown component of the 2D x-ray image. Adjusting the 2D contour may generate data that may be used to calibrate the scan model. One or more parameters of the scan model may be adjusted during calibration. A new 2D contour may be generated based on the calibrated scan model. The new 2D contour may be overlaid on the 2D x-ray image. Then, the root component of the 2D contour may be adjusted to align with the corresponding root component of the 2D x-ray image. Once the root component of the 2D contour has been aligned to the corresponding root component in the 2D x-ray image, the 3D tooth model may be adjusted based on the data obtained from adjusting the root component of the 2D contour. The resultant 3D tooth model may be an accurate 3D model of the patient's complete tooth. This process may be performed for multiple teeth to generate an accurate model of a patient's upper and lower arches.

Embodiments described herein are discussed with reference to intraoral scanners, intraoral images, intraoral scan sessions, and so forth. However, it should be understood that embodiments also apply to other types of scanners than intraoral scanners. Embodiments may apply to any type of scanner that takes multiple images and stitches these images together to form a combined image or virtual model. For example, embodiments may apply to desktop model scanners and so forth. Additionally, it should be understood that intraoral scanners or other scanners may be used to scan objects other than dental sites in an oral cavity. Accordingly, embodiments describing intraoral images should be understood as being generally applicable to any types of images generated by a scanner, embodiments describing intraoral scan sessions should be understood as being applicable to scan sessions for any type of object, and embodiments describing intraoral scanners should be understood as being generally applicable to many types of scanners.

Embodiments described herein are discussed with reference to panoramic x-rays, panoramic x-ray images, panoramic images, panoramic radiograph, and so forth. However, it should be understood that embodiments also apply to other types of 2D x-ray images or 2D x-ray images derived from 3D x-ray data. Embodiments may apply to any type of x-ray image generated by any type of radiography equipment. For example, embodiments may apply to panoramic x-rays, bitewing x-rays, cephalometric x-rays, and so forth. Accordingly, embodiments describing panoramic x-ray images should be understood as being generally applicable to any types of x-ray images generated by radiography devices (e.g., radiography equipment), embodiments describing radiography sessions should be understood as being applicable to radiography sessions for any type of object, and embodiments describing radiography devices should be understood as being generally applicable to many types of radiography devices.

It should be noted that for illustrative purposes, the various exemplary methods and systems may be described in connection with a single tooth of a patient; however, it should be understood that such exemplary methods and systems may be suitably implemented on more than one tooth and/or one or more dental arches and/or teeth of a patient, such as molars, bicuspids, canines, upper dental arch, lower dental arch, or any other teeth of a patient.

FIG. 1 illustrates an exemplary system for tooth modeling, in accordance with embodiments of the present invention. In one embodiment, system 100 carries out one or more operations below described in methods 700, 800, 900, 1000, and/or 1100 of FIGS. 7, 8, 9, 10 and 11, respectively. System 100 includes a computing device 114 and may include a data store (not shown).

Computing device 114 may include a processing device, memory, secondary storage, one or more input devices (e.g., such as a keyboard, mouse, tablet, and so on), one or more output devices (e.g., a display, a printer, etc.), and/or other hardware components. Computing device 114 may be connected to a data store either directly or via a network. The network may be a local area network (LAN), a public wide area network (WAN) (e.g., the Internet), a private WAN (e.g., an intranet), or a combination thereof.

A data store may be an internal data store, or an external data store that is connected to computing device 114 directly or via a network. Examples of network data stores include a storage area network (SAN), a network attached storage (NAS), and a storage service provided by a cloud computing service provider.

In some embodiments, a scanner (not shown) for obtaining three-dimensional (3D) and/or two-dimensional (2D) optical data of a dental site in a patient's oral cavity is operatively connected to the computing device 114. The scanner may include a probe (e.g., a hand held probe) for optically capturing three-dimensional structures (e.g., by confocal focusing of an array of light beams). The scanner may be used to perform an intraoral scan of a patient's oral cavity. 3D model application 108 running on computing device 114 may communicate with the scanner to effectuate the intraoral scan. A result of the intraoral scan may be a sequence of intraoral optical images that have been discretely generated (e.g., by pressing on a "generate image" button of the scanner for each image) or an intraoral video, and may be stored as patient data in the data store. Preferably, overlapping of the images or scans of features in the dental site in a patient's oral cavity may be obtained to enable accurate image registration, so that intraoral images may be stitched together to provide a composite 3D crown component (e.g., 3D crown component 104) of a 3D (tooth) model (e.g., 3D model 106).

The computing device 114 may be configured to facilitate any other conventional orthodontic treatment applications, such as methods or processes for tracking teeth movement and position, evaluating gingival effects, or any other orthodontic treatment process from pre-treatment to final stages, or any stages in between. To facilitate modeling of roots and crowns of a patient, computing device 114 may include one or more software algorithms, such as performed by 3D model application 108, configured for generating 3D model 106 of a complete tooth and/or performing other functions set forth herein.

3D model 106 (e.g., 3D model, 3D tooth model, or initial 3D model) may be an initial 3D model 106 of an object, such as a patient's tooth or a dental arch containing multiple teeth of a patient. The initial 3D tooth model 106 may include a 3D root component 102 from a template (e.g., generic component, generic root component, generic 3D root component, or generic tooth model) that may be combined with a corresponding 3D crown component 104 (e.g., tooth crown model) of a patient to yield a complete tooth model, such as initial 3D model 106. 3D root component 102 may be a generic 3D root component for an exemplary tooth. 3D root component may be configured for combination with 3D crown component 104 for the corresponding tooth to yield a complete 3D model 106 for a particular tooth. In one example, 3D root component 102 may be a generic tooth model configured to provide a generic three-dimensional model of a root or both root and crown for a particular tooth of a patient. 3D root component 102 may be of the same type of tooth (e.g. molar, canine, bicuspid and the like) as the actual tooth it is intended to model. In another example, 3D root component 102 may be the same numbered tooth as the actual patient tooth, using conventional tooth numbering and identification systems. The creation of initial 3D model 106 may be suitably realized by an automated morphing of 3D root component 102 and patient 3D crown component 104, such as by a computer algorithm within 3D model application 108. Details of generating the initial 3D model 106 may be further described in reference to FIG. 7.

Returning to FIG. 1, although shown as receiving 3D model 106, the computing device 114 may also be configured for generating 3D root component 102, patient 3D crown component 104, and/or initial 3D model 106. 3D model application 108 may perform the aforementioned. Computing device 114 may store in the data store morphing data and information from 3D root component 102 and 3D crown component 104. The data in the data store may be used to generate a complete 3D tooth model 106. However, the roots of teeth in the 3D tooth model 106 at this point may not correspond to the actual tooth roots of the patient.

Computing device 114 may receive 2D x-ray image 112. The 2D x-ray image 112 may be a 2D x-ray image of a patient's mouth (e.g., of one or more particular teeth of the patient or all teeth of the patient). Initial 3D model 106 may correspond to a tooth (or multiple teeth) in 2D x-ray image 112. Since the 3D crown component 104 is generated from actual patient data, 3D crown component 104 for a tooth may be the same as the corresponding crown component for that tooth depicted in 2D x-ray image 112.

In one example, 2D x-ray image 112 may be a panoramic x-ray image. A panoramic x-ray may be a 2D x-ray that captures a patient's entire mouth as a single image. A panoramic x-ray may capture features including the teeth (crowns and/or roots), upper and lower jaw, surrounding structures and tissue. An example of a panoramic x-ray image is illustrated in reference to FIG. 2D. Returning to FIG. 1, a panoramic image may take images on multiple planes and stitch the images together in a single composite image. The 2D x-ray image 112 may be stored at a data store associated with computing device 114. X-ray imaging devices (e.g., radiography equipment) (not shown), such as panoramic radiography device, may include a horizontal rotating arm which holds an x-ray source (e.g., x-ray camera, x-ray beam) and a moving film mechanism (holding x-ray film) arranged at opposite extremities. The x-ray source rotates around the patient's head emitting radiation and capturing resultant images on x-ray film at the film mechanism. The x-ray image device may include one or more parameters. Parameters may be associated with an x-ray imaging device and used to describe the imaging process (e.g., scanning process) of the particular x-ray imaging device. Parameters of an x-ray imaging device may include a coordinate system parameter, a scan angle parameter, an arch length parameter, and/or an elliptical arch parameter, for example. An exemplary panoramic x-ray imaging device and associated parameters may be further described in reference to FIGS. 2A-D.

Computing device 114 may receive 3D model 106 and 2D x-ray image 112. Computing device 114 may generate a scan model representing an initial estimate of the one or more parameters of the x-ray imaging device. Scan model module 130 may generate the scan model. A scan model may be a mathematical model to simulate the scanning performed by the x-ray imaging device. The scan model may be used to describe the projection of the 3D model (e.g., 3D model 106) into a 2D image that corresponds to an x-ray image (e.g., that corresponds to a panoramic x-ray image). The scan model may also be used to transform 2D image back to the 3D model. The scan model may include one or more parameters, which may correspond to the parameters of an x-ray device that would be used to generate a similar 2D x-ray image. The scan model may use an initial estimate of one or more parameters of the x-ray imaging device. The scan model may be further described in regards to FIG. 2A-D.

Scan model module 130 may generate a 2D contour 116 of 3D model 106. To generate the 2D contour 116, 3D model 106 may be projected onto a plane as a 2D contour 116 by using the scan model, as described above. A 2D contour may be a 2D outline image of a 3D model (e.g., 3D model 106). In one embodiment, generating the 2D contour includes projecting the 3D model onto a plane using the scan model to generate a 2D image. Image processing may be used on the 2D image to create 2D contour 116. The 2D contour 116 may include a crown component 118 and a root component 122. Crown component 118 may be the 2D representation of 3D crown component 104. Root component 122 may be the 2D representation of root component 102. The scan model generated by scan model module 130 may not be based on the actual one or more parameters of the x-ray imaging device that generated 2D x-ray image 112. Accordingly, the scan model may use an initial estimate of one or more parameters of the x-ray imaging device when used to generate 2D contour 116. The generation of the 2D contour may be further described in regard to FIGS. 2A-D.

Once 2D contour 116 is generated, scan model module 130 may overlay the 2D contour 115 onto 2D x-ray image 112 (e.g., overlay 124). 2D contour 116 may be overlaid on the corresponding tooth in the 2D x-ray image 112. The 2D contour 116 may not initially align with corresponding tooth in 2D x-ray image 112 due to incorrect initial estimates for the one or more parameters of the x-ray imaging device. Accordingly, the 2D contour 116 may be adjusted to approximately align with 2D x-ray image 112 (e.g., adjust 126). The adjustment may be an automatic adjustment that is performed using image processing techniques, may be a manual adjustment performed by a user, or may be a combination thereof. In particular, the 2D contour 116 may be adjusted so that crown component 118 approximately aligns with the corresponding crown component of 2D x-ray image 112. Since both the crown component 118 of 2D contour 116 and 2D x-ray image 112 may be from the same actual patient, the crown component 118 may align closely after performing scaling, rotating and/or repositioning of 2D contour 116. The overlay and adjustment of the crown component of the 2D contour may be further described in reference to FIGS. 3A-C.

Once the crown component 118 of 2D contour 116 has been adjusted to approximately align with the corresponding crown component of 2D x-ray image 112, data 124 (e.g., calibration data) from the adjustment may be generated. The calibration data may be from the moving of one or points on 2D contour to approximately align with 2D x-ray image 112 during the adjustment. The calibration data may be sent to scan module 130 and used to calibrate the scan model. Scan model module 130 may use the calibration data to adjust one or more of the initial parameters of the x-ray imaging device used by the scan model. Calibrating the scan model may be further described in reference to FIGS. 3A-C.

Once the scan model is calibrated, scan module 130 may generate a new 2D contour (e.g., new 2D contour 116) using the calibrated scan model. The new two-dimensional contour 116 may be overlaid on 2D x-ray image 112, in a similar manner as discussed above. Since the crown component 118 was previously adjusted, crown component 118 may approximately align with the corresponding crown component of 2D x-ray image 112. Root component 122 of new 2D contour 116 may not align with the corresponding tooth component of 2D x-ray image 112. Accordingly, root component 112 may be adjusted to approximately align with the corresponding tooth component of 2D x-ray image 112. This adjustment may be performed automatically, manually based on user input, or a combination thereof. Additional data (e.g., root adjustment data) from adjusting root component 122 of new 2D contour 116 may be sent to computing device 114. Scan model module 130 may use the additional data to adjust the 3D root component 102 of 3D model 106 based on the adjustments made to root component 122 of the new 2D contour 116. Alternatively, adjustments may be made to the 3D model 106, and new 2D contours may be generated and projected onto the x-ray to show whether the new 2D contours align with the 2D x-ray. This may be performed incrementally over multiple iterations. Accordingly, scan model module 130 may generate a virtual model (not shown) of the patient's tooth that accurately reflects the crown and root of the patient's tooth. Adjustment of the root component may be further described in reference to FIGS. 4A-C and 5A-B. The virtual model may be further described in reference to FIG. 6.

Figure 2A:
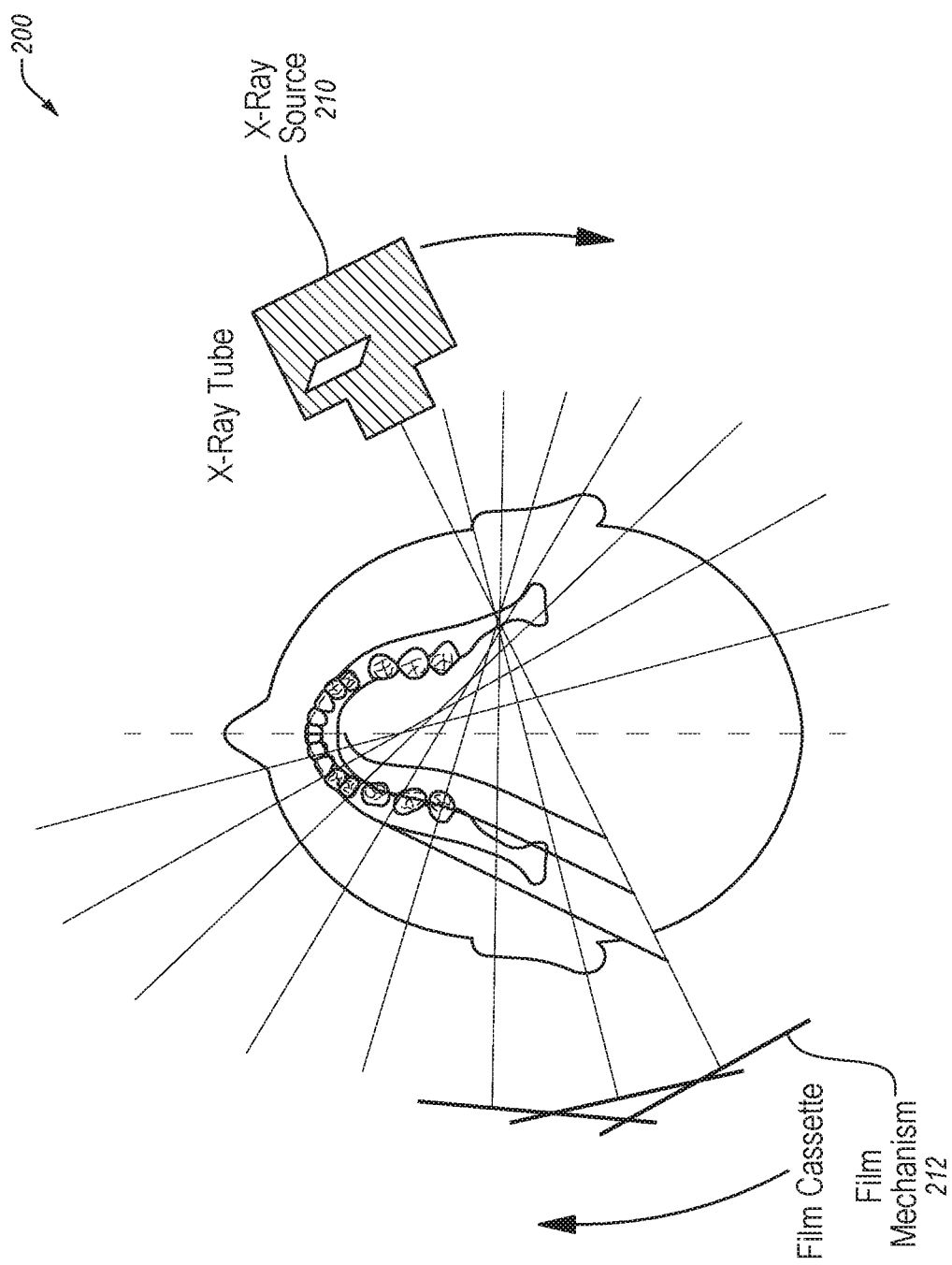
FIG. 2A illustrates a diagram of a panoramic image process for panoramic x-ray imaging device, in accordance with embodiments of the present invention.
Figure 2B:
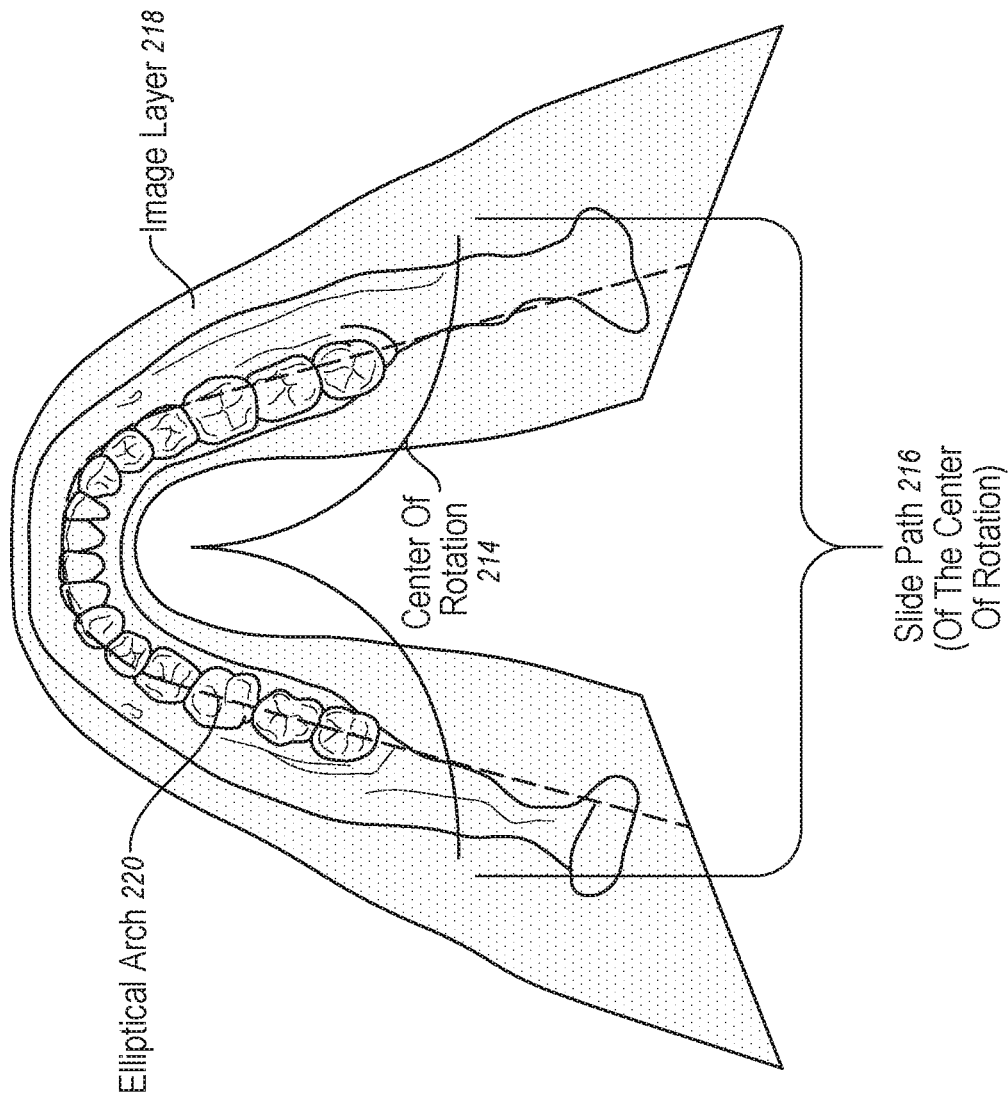
FIG. 2B illustrates a diagram of features of the panoramic image process of FIG. 2A, in accordance with embodiments of the present invention.

FIG. 2A illustrates a diagram of a panoramic image process for a panoramic x-ray imaging device, in accordance with embodiments of the present invention. An x-ray imaging device, such as panoramic x-ray imaging device 200, may include an x-ray source 210 and a film mechanism 212. In a panoramic image process, x-ray source 210 rotates around the patient's head, emitting radiation that may be limited to a narrow vertical beam by a lead collimator at the front of the x-ray source 210. The film mechanism 212 may simultaneously pass on the opposite side of the patient's head. Film mechanism 212 may include a film cassette holder that may contain x-ray film and a lead shield. Alternatively, film mechanism 212 may be an electronic x-ray detector. The film mechanism 212 may move in the same rotational direction as the x-ray source 210. The rate of motion of film mechanism 212 may be correlated with the rate of the motion of x-ray source 210 as the x-ray beam sweeps through the patient's tissues and equalizes the vertical and horizontal magnification of certain structures. A center of rotation (e.g., center of rotation 214 of FIG. 2B) may be the point around which the x-ray source 210 and film mechanism 212 rotate, as illustrated in FIG. 2B. FIG. 2B will be described to help describe panoramic image process of panoramic x-ray image device 200.

FIG. 2B illustrates a diagram of features of the panoramic image process executed by panoramic x-ray device 200 of FIG. 2A, in accordance with embodiments of the present invention. The rotation of the x-ray source 210 and film mechanism 212 create a continuously moving rotation center such as center of rotation 214. Sliding path 216 of the center of rotation illustrates the path of the moving rotation center as the x-ray source 210 rotates around the patients head. An elliptical arch 220 may be a plane where vertical and horizontal magnifications are equalized by the speed of the moving film. Features on the elliptical arch 220 may be projected as sharp and undistorted points in an x-ray image. The further away from elliptical arch 220 the points in a patient's tissue are, the more blurred and distorted they appear on the x-ray image. A certain amount of blurring and distortion may be acceptable. However, some structures may be so far from elliptical arch 220 that they become too blurred and distorted to be useful. A limited area on either side of the elliptical arch 220 may be imaged with sufficient sharpness and dimensional accuracy to render features recognizable. An image layer 215 represents an area around elliptical arch 220 where structures within the area may be projected with sufficient clarity and sharpness. A patient's head may be positioned in panoramic x-ray imaging device 200 so that the teeth and jaws are located in image layer 215.

The actual location and contour of image layer 215 may be determined by the design of a panoramic x-ray imaging device.

Figure 2C:
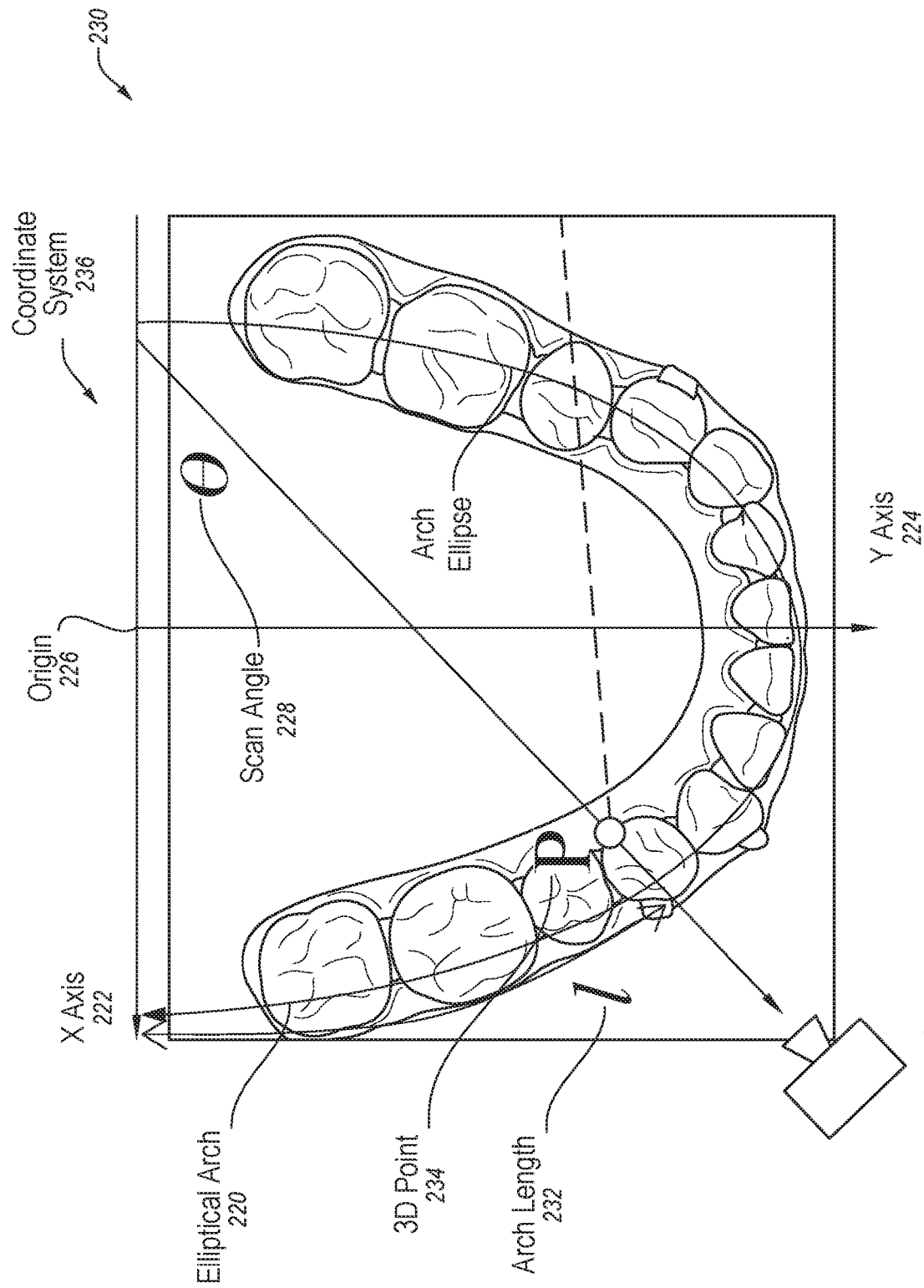
FIG. 2C illustrates parameters of a panoramic x-ray imaging device of FIG. 2A used in a scan model, in accordance with embodiments of the present invention.

FIG. 2C illustrates parameters of a panoramic x-ray imaging device of FIG. 2A used in a scan model, in accordance with embodiments of the present invention. Scan model 230 may be a scan model of panoramic x-ray imaging device 200 of FIG. 2A. A scan model may be a mathematical model to simulate the scanning by the x-ray imaging device. Scan model 230 may be used to describe the projection of the 3D model (e.g., 3D model 106) into a 2D image. The scan model may also be used to transform a 2D image back to a 3D model. Scan model may be generated by scan model module 130 of FIG. 1. The scan model 230 may include one or more parameters. Parameters may be associated with an x-ray imaging device and used to describe the imaging process (e.g., scanning process) of the x-ray imaging device. For purposes of illustration, scan model 230 may be described as a scan model of a panoramic imaging device. It should be noted a scan model may be used to describe any type of x-ray imaging device and/or different scan models may be used to describe the same x-ray imaging device. Additionally, the parameters of the scan model may be specific to an individual x-ray imaging device or type of x-ray imaging device. Accordingly, the scan model and parameters described herein are merely illustrative and are not intended to be limiting.

Parameters of a panoramic x-ray imaging device 200 may include a coordinate system 236, elliptical arch 220, scan angle 228, arch length 232, and one or more points (e.g., 3D point 234) in 3D space. Coordinate system 236 may be a 3D Cartesian coordinate system. Coordinate system 236 may include an X-axis 222, a Y-axis 224, a Z-axis (not shown), and an origin 226. The coordinate system 236 may be used to locate points (e.g., 3D point 234) in 3D space. Another parameter of a panoramic x-ray imaging device 200 may include elliptical arch 220 (e.g., arch ellipse, curved plane), as discussed in reference to FIG. 2B. Another parameter of panoramic x-ray imaging device 200 may include scan angle 228. Scan angle 228 may be an angle of the x-ray source 210 relative to the coordinate system at a point in time during a scan. Arch length 232 may be the length of a part of elliptical arch 220. The part of elliptical arch 220 may include a distance from an axis of the coordinate system to a point on elliptical arch 220 where the x-ray beam of x-ray source 210 intersects elliptical arch 220. 3D point 234 may be any point, such as point P, in 3D space. One or more parameters of panoramic x-ray imaging device 200 may be used to generate scan model 230. An example of scan model 230 is described as follows:

Elliptical arch 220 may be defined as:

$$\left(\frac{x}{r_x}\right)^2 + \left(\frac{y}{r_y}\right)^2 = 1 \quad (1)$$

where x is the x-coordinate of 3D point 234 (P), $r_x$ is the radius from origin 226 to where X-axis 222 intersects elliptical arch 220, y is the y-coordinate of 3D point 234 (P) and $r_y$ is the radius from origin 226 to where the Y-axis 224 intersects elliptical arch 220.

Any point, P (e.g., 3D point 234), in 3D space may be described by the position of the point in coordinate system 236 as:

$$P = (P_x, P_y, P_z)^T \quad (2)$$

where $P_x$ is the x-coordinate of a point on coordinate system 236, $P_y$ is the y-coordinate of a point on coordinate system 236, $P_z$ is the z-coordinate of a point on coordinate system 235, T is a transpose of a vector or matrix. It should be noted that T in the below equations are also a transpose of a vector or matrix unless otherwise noted.

Scan angle 228 (θ) may be described as:

$$\theta = \tan^{-1}\left(\frac{P_y/r_y}{P_x/r_x}\right) \quad (3)$$

where $P_x$, $r_x$, $P_y$, $r_y$ are described above.

Arch length 230 (l), may start from X-axis 222 and be described as:

$$l = \int_0^\theta dl(\theta) d\theta \quad (4)$$

where θ is the scan angle 228, dl(θ) is derivative of l over scan angle θ, and dθ is the derivative of θ.

Relative arch length, t, may be described as:

$$t = \frac{l}{l_0} \quad (5)$$

where l is arch length 230 and $l_0$ may be the total length of elliptical arch 220 from the positive X-axis 222 to the negative X-axis 222.

A 3D point, such as 3D point 234 (P), may be projected into a 2D point $p = (p_x, p_y)^T$ in x-ray image. $p_x$ is the x-coordinate of image (from left to right) and can computed by a polynomial such as the following:

$$p_x = \Sigma_{i=0}^n a_i t^i \quad (6)$$

where n is the degree of polynomial, normally between 2 to 5. $a_i$ is a coefficient and t is the relative length in equation (5). $p_y$ is the y-coordinate of image (from top to bottom) and can also be computed from similar polynomial of $P_z$ $$p_y = \Sigma_{i=0}^m b_i P_z^i \quad (7)$$

where m is the degree of polynomial, normally between 1 to 3. $b_i$ is a coefficient and $P_z$ is the z-coordinate of a point on coordinate system 235.

One or more parameters of panoramic x-ray imaging device 200 may or may not be known by scan model module 130. For parameters that are not known, scan model module 130 may use an initial estimate of one or more parameters to generate scan model 230. For example, the position of coordinate system 236 may be estimated from the tooth position of a jaw. The Z-axis of coordinate system 236 may be estimated to be in the normal direction of the occlusal surface, which is a plane that passes the tips of the one or more of the lower teeth. Y-axis 224 may be estimated to separate the teeth into two halves. Origin 226 may be estimated to be at a position that is approximately the average of all the teeth in the jaw of the patient. Origin 226 may be estimated as 20-25 mm from the first molar of the upper or lower arch form. Additional estimates may include the following:

Using coordinate system 236, any point, Q, in space (e.g., real world) may be projected as a 3D point, P in coordinate system 236 by equation 10 below:

$$Q = (Q_x, Q_y, Q_z)^T \quad (8)$$

where $Q_x$, $Q_y$, $Q_z$ are respectively x, y, z coordinates of a point on the world space.

$$P = (P_x, P_y, P_z)^T \quad (9)$$

where $P_x$, $P_y$, $P_z$ are respectively x, y, z coordinates of a point on coordinate system 236.

$$P = R \cdot Q + T \quad (10)$$

where (R,T) is the rigid transformation from the real world into coordinate system 236.

Elliptical arch 220 (J) may be estimated using points representing the center of one or more crowns in the jaw by, for example, minimizing a cost function (minimization), as illustrated as follows:

$$\min_{a,b} J = \min_{a,b} \sum_{i=1}^{n} (a \cdot P_{ix}^2 + b \cdot P_{iy}^2 - 1)^2 \quad (11)$$

where ($P_{ix}$, $P_{iy}$, $P_{iz}$) is be the ith crown center in coordinate system 236, n is the number of crown center used. a, b are the coefficients to be minimized.

The radius in the X-axis 222 direction and the Y-axis 224 direction may be estimated as follows from the coefficients a, b in eq (11):

$$r_x = \frac{1}{\sqrt{a}} \quad (12)$$

$$r_y = \frac{1}{\sqrt{b}} \quad (13)$$

Additionally, variables of the polynomial curve function, described above, may be estimated as linear and/or estimated from a digital x-ray image, such as a digital panoramic x-ray image.

Figure 2D:
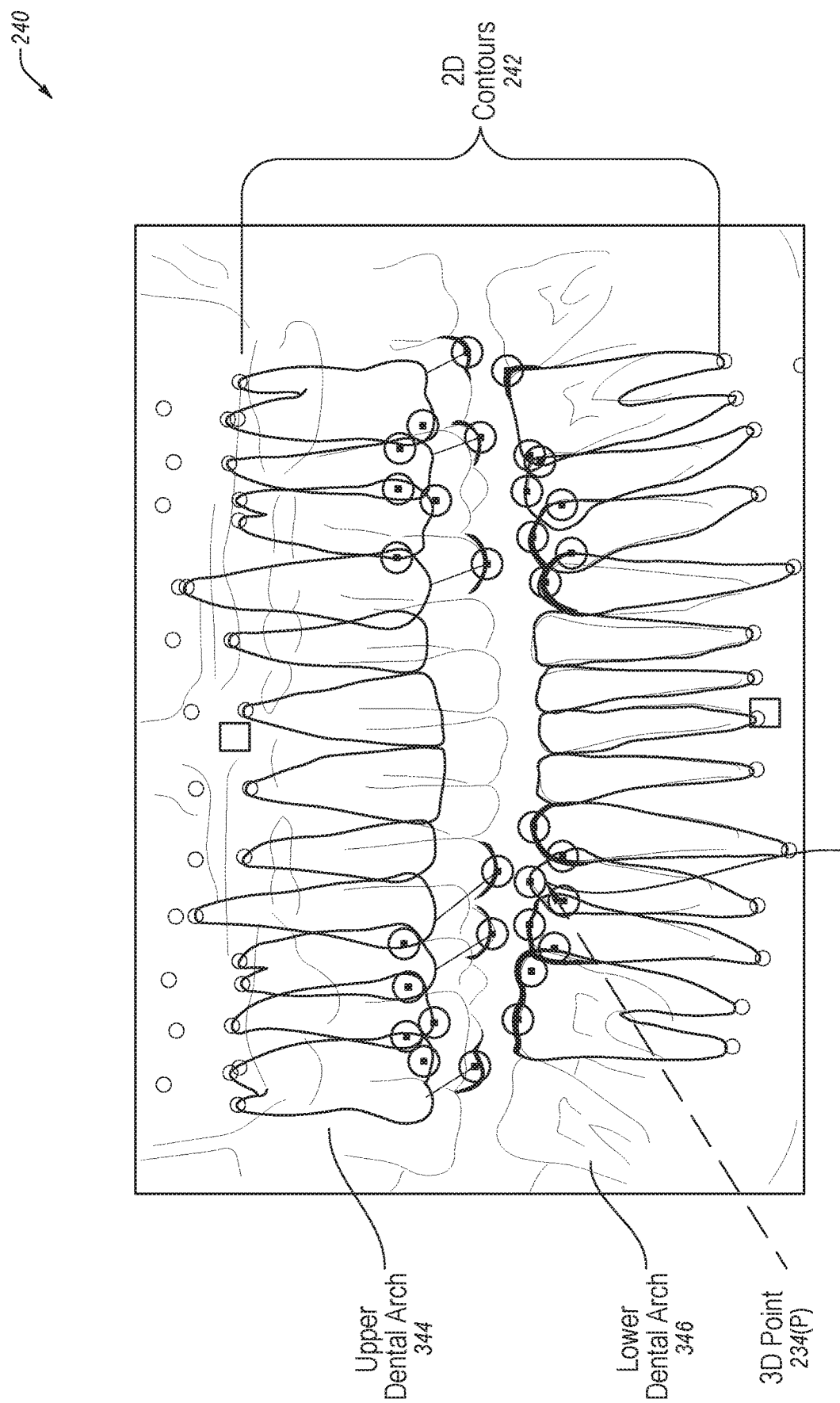
FIG. 2D illustrates a projection of a two-dimensional contour generated from a 3D model onto a 2D panoramic x-ray image, in accordance with embodiments of the present invention.

FIG. 2D illustrates a projection of a two-dimensional contour generated from a 3D model onto a 2D panoramic x-ray image 240, in accordance with embodiments of the present invention. Panoramic x-ray image 240 illustrates a panoramic x-ray image of the mouth of a patient. 2D contours 242 have been overlaid onto panoramic x-ray image 240, with teeth of 2D contours 242 approximately overlaid onto corresponding teeth in the panoramic x-ray image 240. 3D point 234 (P) (a point in 3D space) of FIG. 2C is shown as projected as a 2D point 238 (p) (a point in 2D space) on the corresponding 2D contour. 3D point 234 (P) may be projected onto a plane as a 2D point 238 (p) using scan model 230 as described in reference to FIG. 2C. Accordingly, a 3D model, such as 3D model 106 of FIG. 1, may be projected as a 2D contour using scan model 230. A 3D model may include multiple 3D points, each of which may be projected as 2D points using scan model 230. The projected 2D points may form the 2D contour, such a 2D contour of one or more teeth.

In one embodiment, one or more of the 2D contours 242 may be generated by projecting the 3D model (e.g., 3D model 106) onto a plane as one or more corresponding 2D images using the scan model 230. The one or more 2D contours 242 may be created by performing image processing on the one or more corresponding 2D images.

Panoramic x-ray image 240 includes upper dental arch 344 and lower dental arch 346. Each dental arch includes multiple teeth and corresponds to the upper and lower dental arch of a patient, respectively. 2D contours 242 includes a distinct 2D contour of each tooth in upper dental arch 344 and lower dental arch 346. Each 2D contour may be generated from a different 3D model corresponding to each of a patient's teeth, or may be generated from a different portion of the same 3D model. Each 2D contour may be generated using a scan model, such as scan model 230.

FIGS. 3A-C illustrate various steps in alignment of a crown portion of a 2D contour generated from a 3D model onto crown portion of a 2D x-ray image, in accordance with embodiments. FIG. 3A illustrates a crown component of a two-dimensional contour overlaid on an x-ray image, in accordance with embodiments of the present invention. 2D contour 302 includes crown component 304. The root component of 2D contour 302 is not shown. 2D contour 302 may be overlaid on 2D x-ray image 306. 2D x-ray image 306 may be part of a panoramic x-ray image. When a 2D contour, such as 2D contour 302, is initially overlaid on 2D x-ray image 306, the 2D contour may not align with the corresponding crown component on 2D x-ray image 306. 2D contour 302 may be adjusted to align with the corresponding crown component on 2D x-ray image 306.

FIG. 3B illustrates adjustment of a crown component of the two-dimensional contour of FIG. 3A, in accordance with embodiments of the present invention. The 2D contours, such as 2D contour 302, may include feature points, such as feature points 308 and 312. 2D point 238 may be a feature point. A feature point may be a 3D point on a 3D model that is projected onto a corresponding 2D contour. A feature point may represent an actual feature on a patient's tooth. A feature point may be of a distinct tooth feature, such as tip of a crown, a crack in a tooth, a filing, an adhesive object, etc., that may be distinguished in an x-ray image, such as 2D x-ray image 306. For example, a feature point may be a prominent feature of the tooth and/or close to the edge of the 2D contour. A feature point on a 3D model (e.g., 3D model 106) may be detected by computer processing, such as scan model module 106. A feature point on a 3D model may be detected manually by a user. Each 2D contour, and each crown component of each 2D contour, may have multiple feature points. For example, the crown component of a 2D contour of a molar may include three feature points and the crown component of a 2D contour of a premolar or incisor may have two feature points. A 2D contour may have any number of feature points. Since the crown component, such as crown component 304, may be generated from a 3D crown component from an actual patient and the x-ray image is also of the same patient, the feature points of the 2D contour may closely align with the corresponding features on the 2D x-ray image.

The crown component 304 may be adjusted to align with the corresponding crown component of 2D x-ray image 306. In particular, the feature points such as 2D point 238 and/or feature point 308 may be adjusted to align with the corresponding feature points of the crown component in 2D x-ray image 306. Adjustment cursor 310 illustrates a cursor that may be used by a user to manually adjust the 2D contour 302 by scaling and/or repositioning the 2D contour 302 so the crown component 304 aligns with the corresponding crown (e.g., crown component) of 2D x-ray 306. In an alternative embodiment, computer processing may be used to automatically adjust the 2D contour 302 by scaling and/or repositioning the 2D contour 302 so the crown component 304 aligns with the crown of 2D x-ray 306. In another embodiment, an auto snap feature may allow a user to move a feature point of 2D contour 302 roughly near the corresponding feature of the corresponding crown of 2D x-ray 306. Computer processing performed by scan model module 130 may then move the feature point (e.g., 2D point 238) to a corresponding match position on 2D x-ray image 306, as illustrated in FIG. 3C. Returning to FIG. 3B, when a feature point is adjusted the entire contour, such as 2D contour 302, may be moved with the feature point. For purposes of illustration, the adjustment of a single contour has been discussed. However, it should be noted that more than one 2D contour (e.g., at least two distinct 2D contours) may be adjusted, either separately or together.

FIG. 3C illustrates calibration of a scan model based on data from adjusting the crown component of a two-dimensional contour of FIG. 3B, in accordance with embodiments of the present invention. Once one or more feature points are adjusted to approximately align with corresponding feature points on the 2D x-ray image 306, the scan model, such as scan model 230, may be calibrated. Scan model 230 may be calibrated by scan model module 130. Data (e.g., calibration data) obtained from adjusting the crown component of one or more 2D contours may be used to calibrate the scan model 230. One or more parameters of scan model 230 may be adjusted using the calibration data. Calibrating the scan model 230 may include adjusting at least one of the coordinate system 236, scan angle 228 ($\theta$), arch length 232 (l), or elliptical arch 220 parameters of x-ray imaging device 200. Calibration may be performed one or more times. Calibration data from adjusting one or more 2D contours (e.g., distinct two dimensional contours) may be used to calibrate scan model 230. Additionally, an adjustment of one or more crown components of the 2D contour followed by calibration may be iterated one or more times. An illustrative example of calibrating one or more parameters (e.g., coordinate system 236, scan angle 228 ($\theta$), arch length 232 (l), elliptical arch 220) of scan model 230 is provided below.

Coordinate system 236 may be adjusted using calibration data as follows:

A position in the real world of point $Q_i$ may be converted to a point $P_i$ on the 3D coordinate system 236 as:

$$P_i = (P_{ix}, P_{iy}, P_{iz})^T \quad (14)$$

where ($P_{ix}, P_{iy}, P_{iz}$) may be the ith crown center in coordinate system 236

For the 3D $P_i$, such as an adjusted feature point, a corresponding point in 2D after adjustment is $p_i = (p_{ix}, p_{iy})^T$. From $p_{iy}$, a Z-coordinate position $P_{iz}'$ may be calculated by solving the following polynomial function:

$$p_{iy} = \Sigma_{j=0}^{m} b_j (P_{iz}') \quad (15)$$

where $b_j$ is known, either from an initial value, or already calibrated in later procedure.

The 3D point, $P_i'$ generated from 2D point, $p_i$, is:

$$P_i' = (P_{ix}, P_{iy}, P_{iz}')^T \quad (16)$$

where $P_{ix}, P_{iy}$ are the same as original $P_i$ in coordinate system 236.

The calibrated coordinate system 236 may be determined by estimating the rigid body transformation (R,T) from all paired 3D points ($P_i, P_i'$), i=1, 2, . . . n. (R,T) is then applied to the original coordinate system to get the calibrated coordinate system.

The polynomial curves for x-coordinates (e.g., x-coordinates for 2D points) and y-coordinates (e.g., y-coordinates for 2D points) may be adjusted using calibration data as follows:

One point $P = (P_x, P_y, P_z)^T$ may be calculated for each feature point Q using the calibrated coordinate system. Point P's corresponding adjusted 2D point is $p = (p_x, p_y)^T$. For each jaw, there may be at least 3 or more such feature point pairs (P,p).

A calibrated scan angle 228 ($\theta$), arch length 232 (l), and relative arch length (t) may be calculated for each feature point P.

The coefficients $a_i$ of equation (6) may be estimated by all paired (t, $p_x$), by an optimization algorithm, such as least square. The equation 6 above is reproduced here:

$$p_x = \Sigma_{i=0}^{n} a_i t^i \quad (6)$$

The coefficients $b_i$ of equation (7) may be estimated by all paired ($P_z, p_y$), by an optimization algorithm such as least square. The equation 7 above is reproduced here:

$$p_y = \Sigma_{i=0}^{m} b_i P_z^i \quad (7)$$

Elliptical arch 220 may be calibrated using the calibrated coordinate system and using the cost function (minimization), equation 11 reproduced below, for all 3D points:

$$J = \Sigma_{i=1}^{n} (a \cdot P_{ix}^2 + b \cdot P_{iy}^2 - 1)^2 \quad (11)$$

Additionally, outlier points may be detected by checking the error between the output of the scan model module 130 and the real, adjusted 2D position. The outlier points may then be removed from calibration pairs to improve model robust and accuracy.

Figures 4A, 4B, 4C:
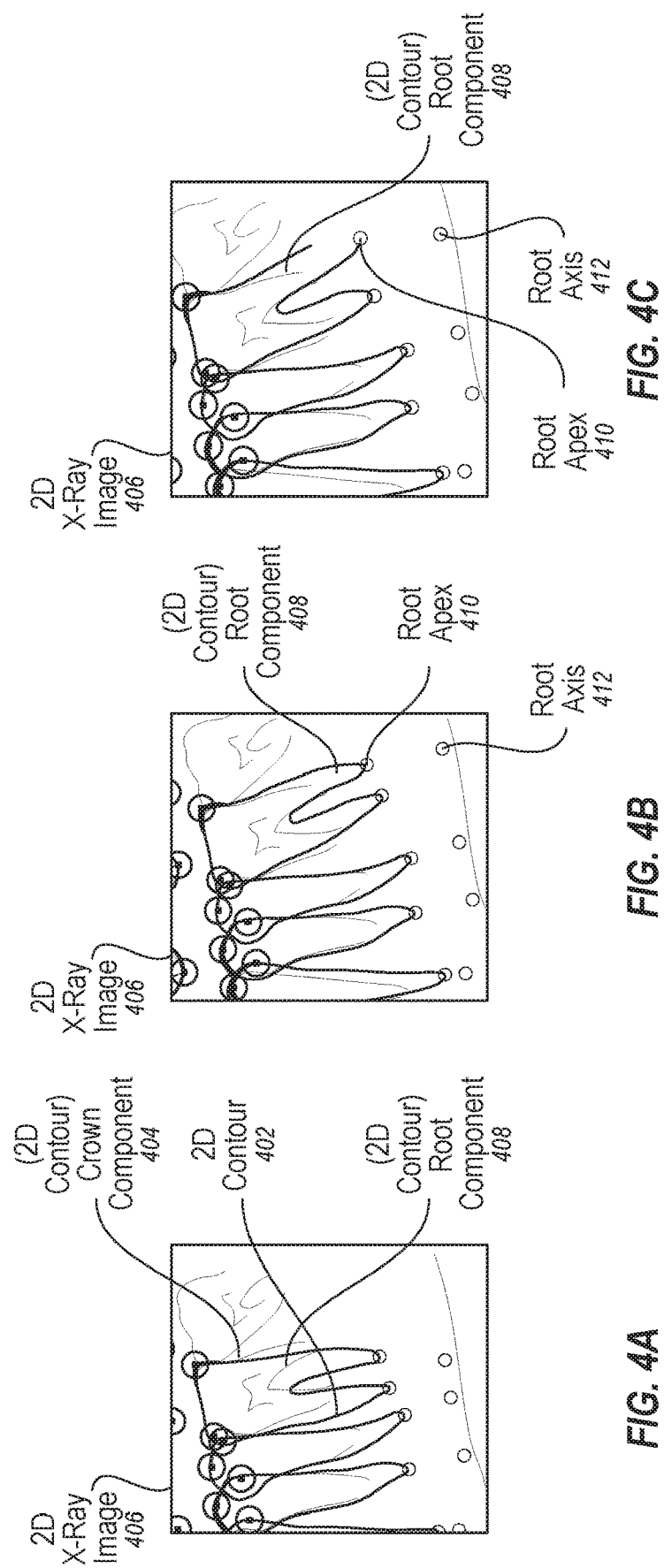
FIG. 4A illustrates a root component of a new two-dimensional contour overlaying an x-ray image, in accordance with embodiments of the present invention.
FIG. 4B illustrates adjustment to a root component of a new two-dimensional contour of FIG. 4A, in accordance with embodiments of the present invention.
FIG. 4C illustrates an adjusted root component of a new two-dimensional contour of FIG. 4B, in accordance with embodiments of the present invention.

FIGS. 4A-C illustrate various steps in alignment of a root portion of a 2D contour generated from a 3D model onto root portion of a 2D x-ray image, in accordance with embodiments. FIG. 4A illustrates a root component of a new two-dimensional contour overlaying an x-ray image, in accordance with embodiments of the present invention. Once scan model 230 has been calibrated, as described in reference to FIGS. 3A-C, a new 2D contour (e.g., 2D contour 402) may be generated by projecting the 3D model (e.g., 3D model 106) using the calibrated scan model (hereinafter, calibrated scan model 230). The new 2D contour 402 may be overlaid onto an x-ray image (e.g., 2D x-ray image 406) in a similar manner as discussed in reference to FIGS. 2D and 3A. The crown component (e.g., crown component 404) of the new 2D contour 402 may approximately align (e.g., match) with the corresponding crown of the x-ray image. The root component (e.g., root component 408) of the new 2D contour 402 may not sufficiently align with the 2D x-ray image 406. The root component 408 may have been generated from a generic 3D root component from a template. Accordingly, the root component 408 may be adjusted to approximately align with the corresponding root component of the x-ray image 406.

FIG. 4B illustrates adjustment to a root component of a new two-dimensional contour of FIG. 4A, in accordance with embodiments of the present invention. Once scan model 230 has been calibrated, as described in reference to FIGS. 3A-C, and a new 2D contour (e.g., 2D contour 402) generated and overlaid onto 2D x-ray image 406, the root component 408 of the 2D contour 402 may be adjusted. Root component 408 may include a root apex 410 and root axis 412. A root apex, such as root apex 410, may be a narrowed end of a root component of a 2D contour of a tooth. A 2D contour of a tooth may have one or more root apexes. A root axis, such as root axis 412, may be or correspond to the position of the root apex (e.g., root apex 410) on the Z-axis of a coordinate system (e.g., coordinate system 236). One or more root apexes (e.g., root apex 410) may be adjusted so that each apex aligns with the corresponding apex of 2D x-ray image 406. One or more axes (e.g., root axis 412 of 2D contour 402) may be adjusted so that each axis may align with the corresponding axis of 2D x-ray image 406. Adjusting root axis 412 of 2D contour 402 may be reflected as an adjustment of the 3D root component (e.g., 3D root component 102) along the Z-axis of the 3D model (e.g., 3D model 106). Root apex 410 and/or root axis 412 may be manually adjusted, adjusted by computer processing (e.g., scan model module 130), or a combination of both. Adjustment of root apex 410 and/or root axis 412 may be performed in any combination, in any order, and/or any number of times.

In another embodiment, once scan model 230 has been calibrated, a new 3D model (e.g., 3D model 106, hereinafter new 3D model 106) may be generated using calibrated scan model 230. The 3D root component (e.g., 3D root component 102) may be adjusted. The adjustment may be performed manually, for example by a user, by computer processing such as by scan model module 130, or a by combination of both. The adjustment of the 3D root component 102 may be performed in a similar manner as described in reference to FIG. 3B. After adjusting the 3D root component 102, a new 2D contour (e.g., 2D contour 402) may be generated by projecting the adjusted new 3D model onto a plane using calibrated scan model 230. The new 2D contour 402 may be overlaid onto an x-ray image (e.g., 2D x-ray image 406), in a similar manner as discussed above. The 3D root adjustment and overlay of the corresponding 2D contour 402 onto the 2D x-ray image 406 may be iterated one or more times so that the root component 408 of the 2D contour 402 approximately aligns with the corresponding root of 2D x-ray image 406. Alternatively, after adjusting the 3D root component 102 and projecting the adjusted new 3D model as a 2D contour 402, the 2D contour root component 408 may be adjusted in a similar manner as discussed above. It should be noted that adjustment of the 3D root component of the new 3D model and/or adjustment of the root component of the 2D contour may be performed in any combination, in any order, and/or any number of times.

FIG. 4C illustrates an adjusted root component of a new two-dimensional contour of FIG. 4B, in accordance with embodiments of the present invention. In FIG. 4C, the root axis 412 has been adjusted to approximately align with the corresponding root axis of 2D x-ray image 406. Root apex 410 has also been adjusted to approximately align with the corresponding root apex of 2D x-ray image 406.

Figures 5A, 5B:
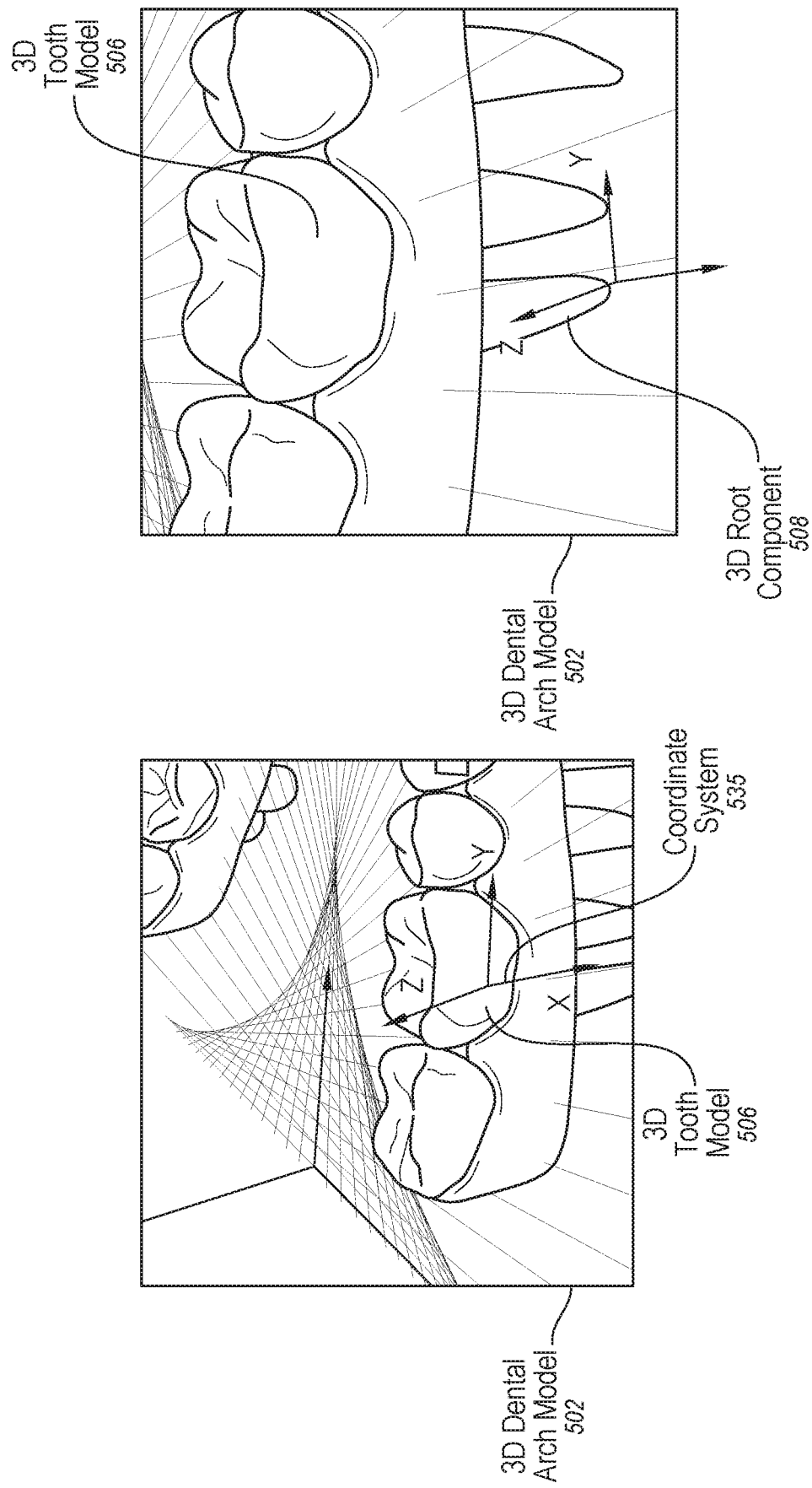
FIG. 5A illustrates a three-dimensional tooth model after adjusting the root component of FIG. 4C, in accordance with embodiments of the present invention.
FIG. 5B illustrates the three-dimensional tooth model of FIG. 5A after adjusting the root component of FIG. 4C, in accordance with embodiments of the present invention.

FIG. 5A illustrates a three-dimensional tooth model after adjusting the root component of FIG. 4C, in accordance with embodiments of the present invention. 3D dental arch model 502 includes 3D tooth model 506 and coordinate system 535. Once the root component has been adjusted as described in FIGS. 4A-C, the coordinate system 535 may be generated for a particular 3D tooth model, such as 3D tooth model 506. The X-axis of coordinate system 535 may be aligned with the direction of the x-ray source (e.g., scan direction x-ray source 210) by using the scan angle (e.g., scan angle 228). The Z-axis may be the same determined in the calibrated scan model 230. The Y-Z plain of calibrated scan model 230 may be aligned with the image plane of x-ray source (e.g., x-ray source 210). Scan model module 130 may perform the operations described in reference to FIG. 5A.

FIG. 5B illustrates the three-dimensional tooth model of FIG. 5A after adjusting the root component of FIG. 4C, in accordance with embodiments of the present invention. Once the coordinate system 535 has been generated for 3D tooth model, as described in reference to FIG. 5A, the adjustment of 2D root component 408 (as described in reference to FIG. 4A-C) may be converted into corresponding adjustments of the 3D root component 508 of 3D tooth model 506. For example, the adjustment of 2D root component 408 may be converted to corresponding adjustments along the Y-Z plane of 3D tooth model 506. In one example, no adjustment along the X-axis is made. Each root component of each tooth in the 3D model, such as 3D dental arch model 502, may be adjusted in a similar manner until all the root components of the 3D model are adjusted.

Figure 6:
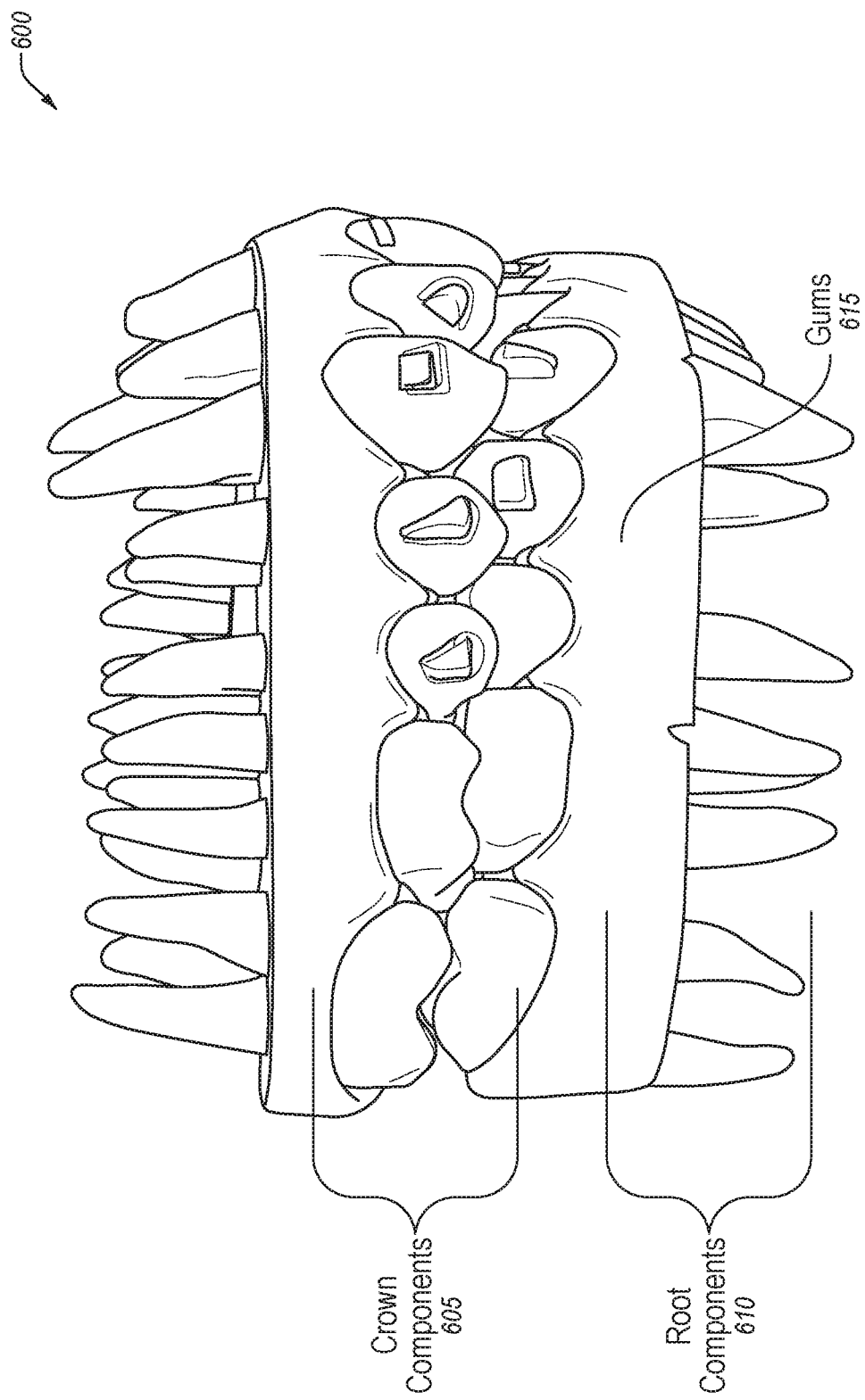
FIG. 6 is an example of a three-dimensional model of a jaw, generated in accordance with embodiments of the present invention.

FIG. 6 is an example of a three-dimensional model of a jaw, generated in accordance with embodiments of the present invention. 3D model 600 illustrates a 3D model of a patient jaw after adjusting one or more 3D root components as described in reference to FIGS. 5A-B. 3D model 600 may be a virtual model. Although 3D model 600 illustrates an entire jaw (e.g., dental site), 3D model may be all or part of the dental site. 3D model 600 includes both the crown components 605 and root components 610 of teeth as well as partial gums 615. 3D model 600 may be manipulated to view the dental site at different angles. 3D model 600 may also be manipulated to add or subtract different layers. In 3D model 600, the jaw bone has been removed. Additionally, the gums may be removed. 3D model 600 may be manipulated to add the jaw bone or any other features of the dental site. By including implementations of the present disclosure, crown components 605 and root components 610 of 3D model 600 may accurately reflect the geometry of a patient's teeth.

Figure 7:
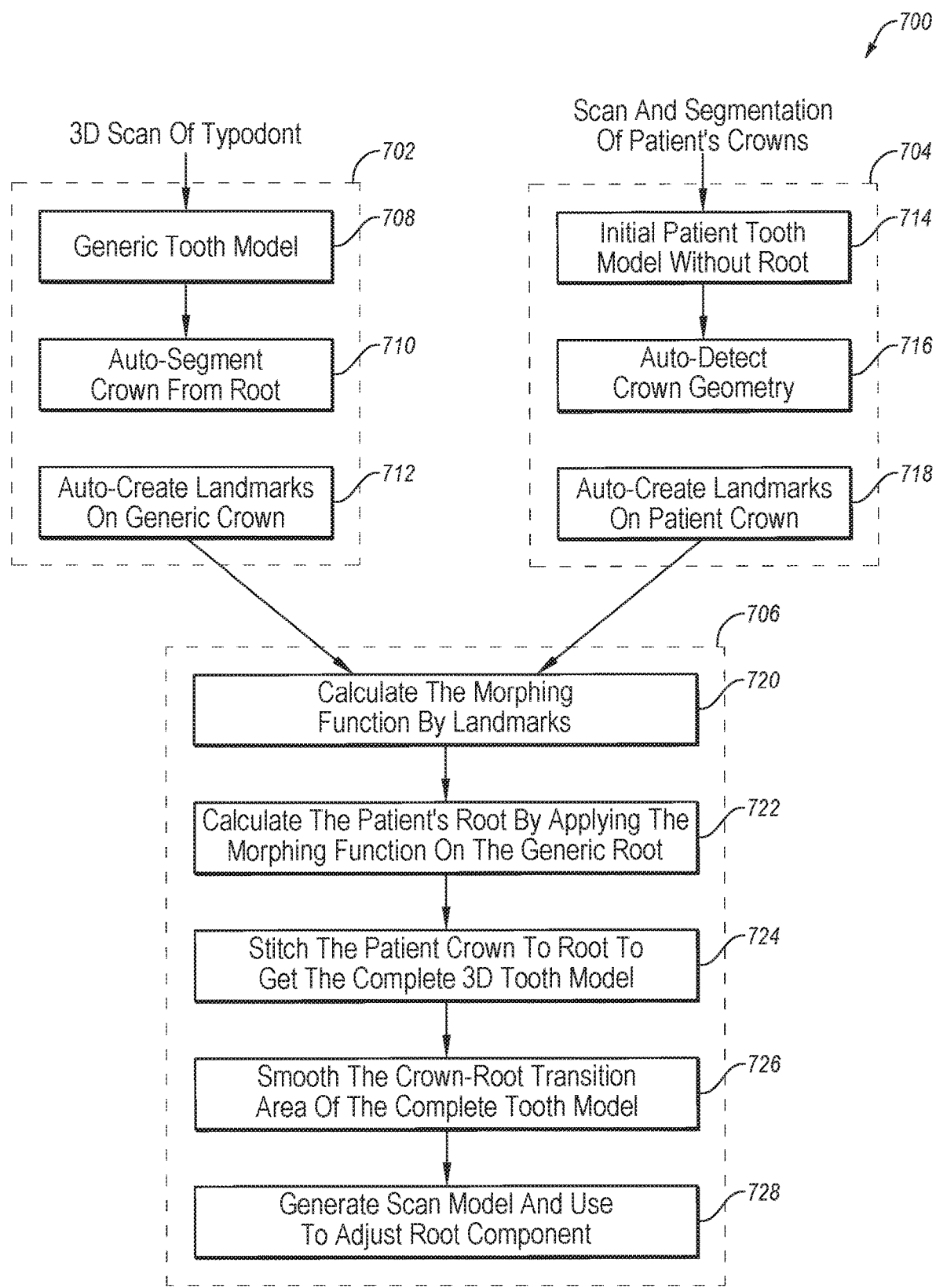
FIG. 7 illustrates a flow diagram for an exemplary method of generating an initial three-dimensional tooth model, in accordance with embodiments of the present invention.

FIG. 7 illustrates a flow diagram for an exemplary method of generating an initial three-dimensional tooth model, in accordance with embodiments of the present invention. Method 700 may include method 702 for generating a generic tooth model (e.g., 3D root component 102), method 704 for generating a patient tooth crown model (e.g., 3D crown component 104), and a method 706 for generating a complete tooth model (e.g., initial 3D model 106) through combination of a morphed generic root model with a corresponding patient tooth crown model. Method 700 may be utilized to provide both generic tooth models and patient tooth crown models for each tooth of a patient and enable a complete tooth model for any and/or all teeth of a patient to be obtained for facilitating orthodontic treatment.

Method 700 may be performed by processing logic that may comprise hardware (e.g., circuitry, dedicated logic, programmable logic, microcode, etc.), software (such as instructions run on a processing device), firmware, or a combination thereof. In one implementation, method 700 may be performed by computer device 114 of FIG. 1. In another implementation, method 700 may be performed or caused to be performed all or in part by 3D model application 108 or scan model module 130 of FIG. 1. For simplicity of explanation, method 700 is depicted and described as a series of acts. However, acts in accordance with this disclosure can occur in various orders, concurrently, and/or with other acts not presented or described herein. Furthermore, not all illustrated acts may be required to implement method 700 in accordance with the disclosed subject matter. In addition, those skilled in the art will understand and appreciate that method 700 may alternatively be represented as a series of interrelated states via a state diagram or interrelated events.

Method 702 begins at block 708 where processing logic implementing the method may generate a generic tooth model template. A generic tooth model template may be configured to facilitate the creation of landmarks on the generic tooth model (e.g., 3D root component 102), to allow for morphing with the patient tooth crown model (e.g., 3D crown component 104). For example, in order to generate adequately distributed landmarks and to accurately segment the crown from the tooth, the setup of generic teeth data may be provided to generate a generic tooth template. The process for generating of a generic tooth model template may include the acquisition of data from a physical tooth model, the decimating of tooth model data, the setting up a generic tooth coordinate system, the constructing of a generic tooth digital model, the identifying of gingival curves, and the creating of template file(s) associated with the generic teeth. The acquisition of data from a physical tooth model data may include the scanning of a standard typodont or any other three-dimensional models for demonstrating alignment of teeth within a patient to generate three-dimensional digital template data.

A typodont or models that are used for scanning may include both an exemplary root and/or crown for a single tooth or multiple teeth of a patient. In addition, such typodont or generic models may be suitably provided based on different configurations of teeth, e.g., different sizes, shapes, and/or caps, different types of teeth such as molars, bicuspids or canines, and/or different occlusal patterns or characteristics, e.g., overbite, underbite, skewed or other like misalignment patterns. In one embodiment, the root shape, configuration or component for such typodont models may include the same generic root configuration for all types of teeth. In another embodiment, the root component for such typodont models may include a typical generic root configuration for a type of tooth, e.g., a typical root shape or configuration for molars, bicuspids and/or canines can be provided, based on one type for all patients, or based on whether the patient is a child or adult, male or female, or any other demographic or characteristic that might be associated with different types of teeth. In another embodiment, the root component for such typodont models may include a typical generic root shape or configuration for a specific actual tooth, e.g., a specific root shape for a particular canine tooth can be used with the specific crown shape for that particular canine tooth to generate the typodont model, again based on one configuration for that—particular tooth all patients, or based on different configurations for that specific tooth depending on whether the patient is a child or adult, male or female, or any other demographic or characteristic that might be associated with different types of teeth. Generic models for any type of teeth characteristic or type may be provided and suitably utilized, allowing great flexibility in specializing for different teeth structures, occlusal patterns and characteristics of a patient.

To reduce the amount of data and/or filter out any undesirable data after such acquisition of data from the typodont or generic tooth model, the decimating of data may be conducted, such as the removal or deletion of data or otherwise the finding of optimal data values through the elimination at a constant fraction of the scanning data; however, the decimating of data may also be suitably omitted or otherwise replaced by any filtering or data enhancement techniques.

Whether or not the scanned data is decimated, the developing of a generic tooth coordinate system may be undertaken, such as to setup or develop a generic tooth coordinate system. The generic tooth coordinate system can be set-up automatically and/or adjusted manually, using any conventional or later developed techniques for setting up coordinate systems of an object. Upon generation of a generic coordinate system for a generic tooth, the constructing of a digital generic tooth model including root and/or crown can be conducted for an individual tooth and/or two or more teeth. Such constructing of digital tooth models can comprise any methodology or process for converting scanned data into a digital representation.

After constructing of the generic tooth digital model, the identifying of the gingival curve may be conducted to identify the gum lines and/or root association. Such identification may include any conventional computational orthodontics methodology or process for identification of gingival curves, now known or hereinafter derived.

Having constructed the digital generic tooth model and identified the gingival curve, one or more generic tooth template files may be created including a substantially complete set of teeth of a patient. Such generic teeth templates may be suitably utilized to allow for segmenting of crowns and landmark distribution on the generic teeth. In addition, such generic teeth templates may be utilized for one or more treatments, and/or replaced or updated with other generic teeth templates as desired. Moreover, such generic teeth templates may be created and/or stored for later use, and may be configured for various differences in patients, such as for children-based templates and adult-based templates, with the ability to have a plurality of templates that are specially created for the different types of teeth and related characteristics, sizes, shapes, and occlusal patterns or other features.

After generic teeth templates have been generated, method 702 continues to block 710, where processing logic may segment the generic crown from the generic root within the generic tooth template. The segmenting may prepare the generic tooth template for landmark creation. The crown portion of the generic tooth template may be parceled out and/or identified to allow mapping during landmark processes.

For the generic tooth, the crown and root geometry may be extracted from the generic tooth model. After such extraction or segmentation, the crown/root mesh may be suitably generated. For example, automated crown/root mesh generation may include the construction of the 3D spline curve, where control points on the transition area between the tooth crown and root may be utilized. The projection of the 3D spline curve on the tooth mesh model may be conducted. A calculation of the intersection between the projected curve and the edges of triangle faces of the mesh may then be made to facilitate the construction of new triangles. The three original vertices of the intersected triangle and the two intersection points may be used to construct three new triangles, such as by use of the Delaunay triangulation's max-min angle criterion. After such construction, the re-triangulation of the old intersected triangle and the replacing of the old triangle with the three newly generated triangles may be performed. Upon re-triangulation and replacement, the generation of new crown/root mesh model may be realized by removing all the faces below/above the projected curve, resulting in a segmented generic tooth crown/root.

Method 702 continues to block 712 where processing logic may create landmarks on the generic crown. The creation of landmarks may be performed prior to morphing with the patient tooth crown model (e.g., 3D crown component 104). In one embodiment, landmarks may be created on a crown sphere and then the landmarks may be projected onto a crown surface. For example, a tooth crown may be mapped to a sphere by central projection. The landmarks may be created on the sphere through appropriate distribution on each of a plurality of cross-sections, e.g., cross-sections through the Z-axis, perpendicular to the X-Y plane. A plurality of landmarks may be created on a sphere with appropriate distribution. The number of landmarks may be determined through variables such as the number of planes to be considered while sweeping through the Z-axis, and the number of points selected for each plane. Once landmarks are created on the crown sphere, landmarks may be suitably projected onto the crown surface. Landmarks may also be projected onto a scan of a patient's crown and a generic tooth crown including a root and crown template. Such an automated generation may be facilitated by one or more algorithms performed by system 100, and may be suitably computed for each patient tooth and generic tooth. The plurality of landmarks on generic tooth crown and the corresponding landmarks on the patient tooth crown (e.g., 3D crown component 104) may be used for calculating the morphing function.

Method 704 may begin at block 714, where processing logic performing the method generates a patient tooth crown model (e.g., 3D crown component 104) without a root component. Generating the patient tooth crown model (e.g., 3D crown component 104) may be suitably realized by various methods and techniques, including various conventional scanning techniques' such as intraoral scanning, as described in reference to FIG. 1.

Method 704 continues to block 716, where processing logic detects the crown geometry to prepare the patient tooth crown model (e.g., 3D crown component 104) for creation of landmarks. For the patient tooth crown model (e.g., 3D crown component 104), the crown geometry may be segmented from the entire tooth using any conventional process for segmentation of crowns from teeth. Method 704 continues to block 718, where processing logic creates landmarks on the patient tooth crown model (e.g., 3D crown component 104), in a similar manner as discussed at block 712 of method 702.

Method 706 may be performed after method 702 and method 704 have been completed. Method 700 may generate a complete tooth model (e.g., 3D model 106) by combination/morphing of the generic tooth model (e.g., 3D root component 102) with the corresponding patient tooth crown model (e.g., 3D crown component 104). Method 706 begins at block 720, where processing logic performing the method calculates a morphing function. In one example, calculating the morphing function may include using a thin-plate spline to calculate the morphing function by the created landmarks. Use of such a thin-plate spline may minimize the deformation energy effects, e.g., minimize the degree or extent of bent in the resulting surface between created landmarks.

Method 706 continues at block 722, where processing logic calculates the patient's root by applying the morphing function on the generic root model (e.g., 3D root component 102). In some cases, the patient crown may be quite different from the generic tooth crown. When this occurs, using only the crown landmarks for morphing control may prove insufficient, as the root shape and direction may be difficult to control. In one embodiment, improved morphing control may be realized by creating landmarks on the root central axis. For example, in the first morphing process, the crown landmarks may be utilized to calculate the initial morphing function, which may be used to obtain a morphed central axis. Next, the central axis of the generic tooth (e.g., 3D root component 102) may be moved to be tangent to the morphed central axis. After movement of the central axis of the generic tooth, the repositioned central axis of the generic tooth (e.g., 3D root component 102) may be suitably scaled such that its length is equal to the morphed central axis in the Z-direction. As a result, both the crown landmarks and the root landmarks may be utilized to calculate the final morphing function.

Method 706 continues to block 724, where processing logic may stitch the patient's crown (e.g., 3D crown component 104) to the generic root model (e.g., 3D root component 102) to generate the complete 3D tooth model (e.g., 3D model 106). To facilitate stitching, the crown mesh and the root mesh may be suitably merged. For example, the stitching process may include projecting 3D loops onto the X-Y plane. Since the projected loops may be homogeneous to a circle, the loop vertices may be re-sorted by angle to construct a merged loop. Next, re-triangulation of the crown mesh and the root mesh can be conducted. Upon re-triangulation, the crown mesh and root mesh can be merged to obtain a topologically correct complete tooth mesh.

Method 706 continues to block 726, where processing logic may smooth the crown-root transition area of the complete tooth model (e.g., 3D model 106). For example, after the stitching process, the transition area may not be very smooth. A smoothing algorithm may be used to smooth the stitching. The smoothing algorithm may operate like a filter to remove "noise" from the stitched points within the transition area. For example, the algorithm may identify or target a first point, then observe neighboring points to suitably change or otherwise adjust the first point to smooth out the stitching. The algorithm may be performed for each tooth. Such an algorithm can also comprise various formats and structures for providing the smoothing function.

Method 706 continues to block 728, where processing logic may perform the above described operations of generating a scan model and using that scan model to adjust root components of one or more teeth to update the 3D model. For example, the 3D model (e.g., initial 3D model 106) may be used in conjunction with the various methods disclosed such as methods 800, 900, 1000, and 1100 of FIGS. 800, 900, 1000, and 1100, respectively to create an accurate 3D model of a patient's teeth, including both accurate crown components and accurate root components of those teeth.

Figure 8:
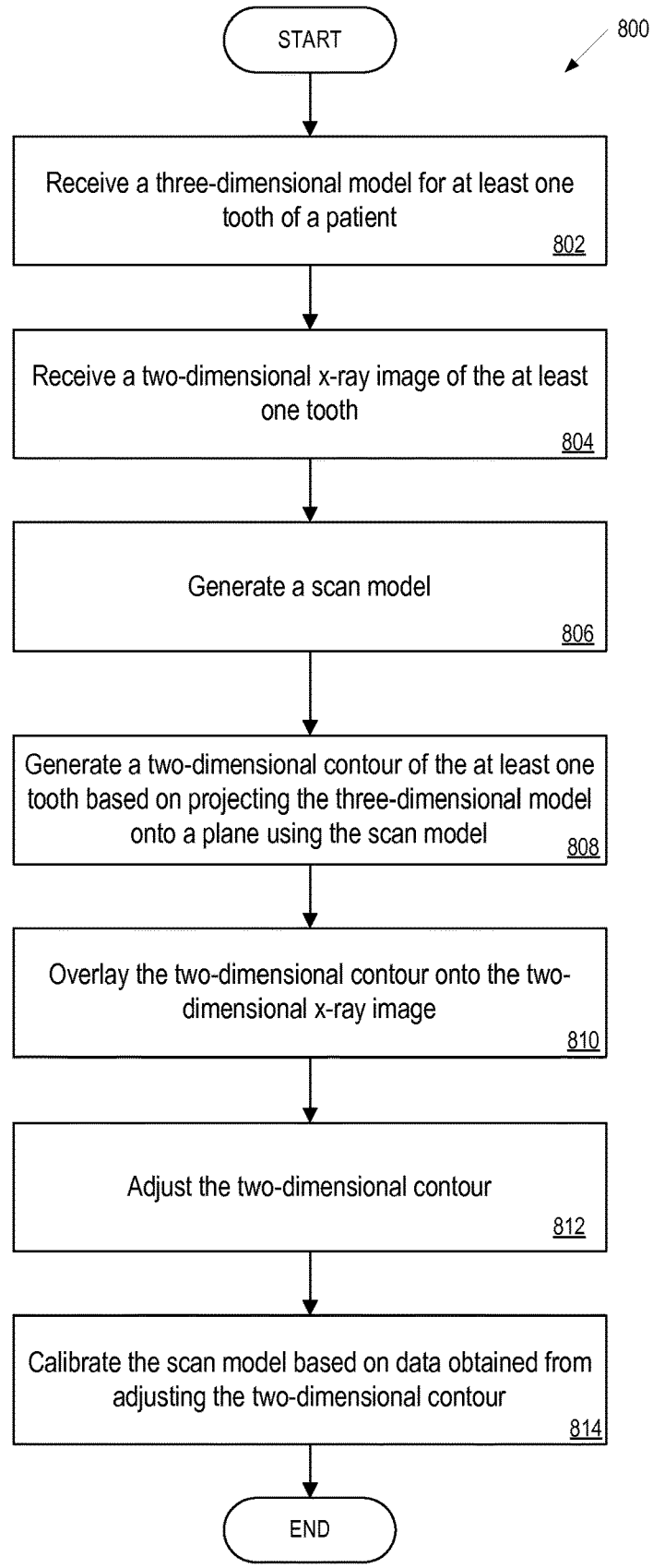
FIG. 8 illustrates a flow diagram for an exemplary method of calibrating a scan model, in accordance with embodiments of the present invention.

FIG. 8 illustrates a flow diagram for an exemplary method 800 of calibrating a scan model, in accordance with embodiments of the present invention. Method 800 may be performed by processing logic that may comprise hardware (e.g., circuitry, dedicated logic, programmable logic, microcode, etc.), software (such as instructions run on a processing device), firmware, or a combination thereof. In one implementation, method 800 may be performed by computer device 114 of FIG. 1. In another implementation, method 800 may be performed or caused to be performed all or in part by 3D model application 108 or scan model module 130 of FIG. 1. For simplicity of explanation, method 800 is depicted and described as a series of acts. However, acts in accordance with this disclosure can occur in various orders, concurrently, and/or with other acts not presented or described herein. Furthermore, not all illustrated acts may be required to implement method 800 in accordance with the disclosed subject matter. In addition, those skilled in the art will understand and appreciate that method 800 may alternatively be represented as a series of interrelated states via a state diagram or interrelated events.

Method 800 begins at block 802, where processing logic performing the method receives a 3D model (e.g., initial 3D model 106) for at least one tooth of the patient. The 3D model (e.g., initial 3D model 106) may be of more than one tooth. For example, the 3D model (e.g., initial 3D model 106) may be of a dental arch including multiple teeth. In one embodiment, the 3D model (e.g., initial 3D model 106) may be generated based on merging the 3D crown component (e.g., 3D crown component 104) from a scan with a template (e.g., 3D root component 102). The initial 3D model may be further described in reference to FIG. 1.

Method 800 continues to block 804, where processing logic receives a 2D x-ray image, such as 2D x-ray image 112, of at least one tooth. An x-ray imaging device that generated the x-ray image (e.g., 2D x-ray image 112) may include one or more parameters. The parameters may describe the scanning process used to generate the 2D x-ray image 112. The x-ray image may be a panoramic x-ray image. Additional details may be described in reference to FIG. 1.

Method 800 continues to block 806, where processing logic generates a scan model. The scan model may represent an initial estimate of one or more parameters of the x-ray imaging device. Additional details of a scan model may be discussed with reference to FIGS. 1 and 2A-D.

Method 800 continues to block 808, where processing logic generates a 2D contour (e.g., 2D contour 116) of at least one tooth based on projecting the 3D model (e.g., initial 3D model 106) onto a plane using the scan model. In one embodiment at least two distinct 2D contours may be generated corresponding to different teeth. In one embodiment, generating a 2D contour (e.g., 2D contour 116) includes projecting a 3D model (e.g., initial 3D model 106) onto a plane using the scan model to generate a 2D image. Image processing may be performed on the 2D image to create the 2D contour (e.g., 2D contour 116). Additional details of generating a 2D contour may be discussed with reference to FIGS. 1, 2C-D, and 3A. Method 800 continues to block 810, where processing logic may overlay the 2D contour (e.g., 2D contour 116) onto the 2D x-ray image (e.g., 2D x-ray image 112). Additional details of overlaying the 2D contour may be discussed with reference to FIGS. 1, 2D, and 3A.

Method 800 continues to block 812, where processing logic adjusts the 2D contour (e.g., 2D contour 116) to cause a first crown component (e.g., crown component 118) of the 2D contour to approximately align to a corresponding crown component of the 2D x-ray image (e.g., 2D x-ray image 112). In one embodiment, processing logic adjusts at least two of distinct 2D contours. In another embodiment, processing logic detects one or more feature points on the 3D crown component (e.g., 3D crown component 104). The crown component of the 2D contour may include projections of these one or more feature points. The 2D contour may be adjusted by scaling and/or repositioning the 2D contour to approximately align with the corresponding crown component of the 2D x-ray image. Additional details of aligning the 2D contour may be discussed with reference to FIGS. 1 and 3A-C.

Method 800 continues to block 814, where processing logic may calibrate the scan model based on data obtained from adjusting the 2D contour (e.g., 2D contour 116). In one embodiment, calibrating the scan model includes adjusting at least one of a coordinate system parameter, scan angle parameter, arch length parameter, or elliptical arch parameter of the x-ray imaging device. In another embodiment, calibrating the scan model may be based on data obtained from adjusting at least two distinct 2D contours. Additional details of calibrating the scan model may be discussed with reference to FIGS. 1 and 3A-C.

Figure 9:
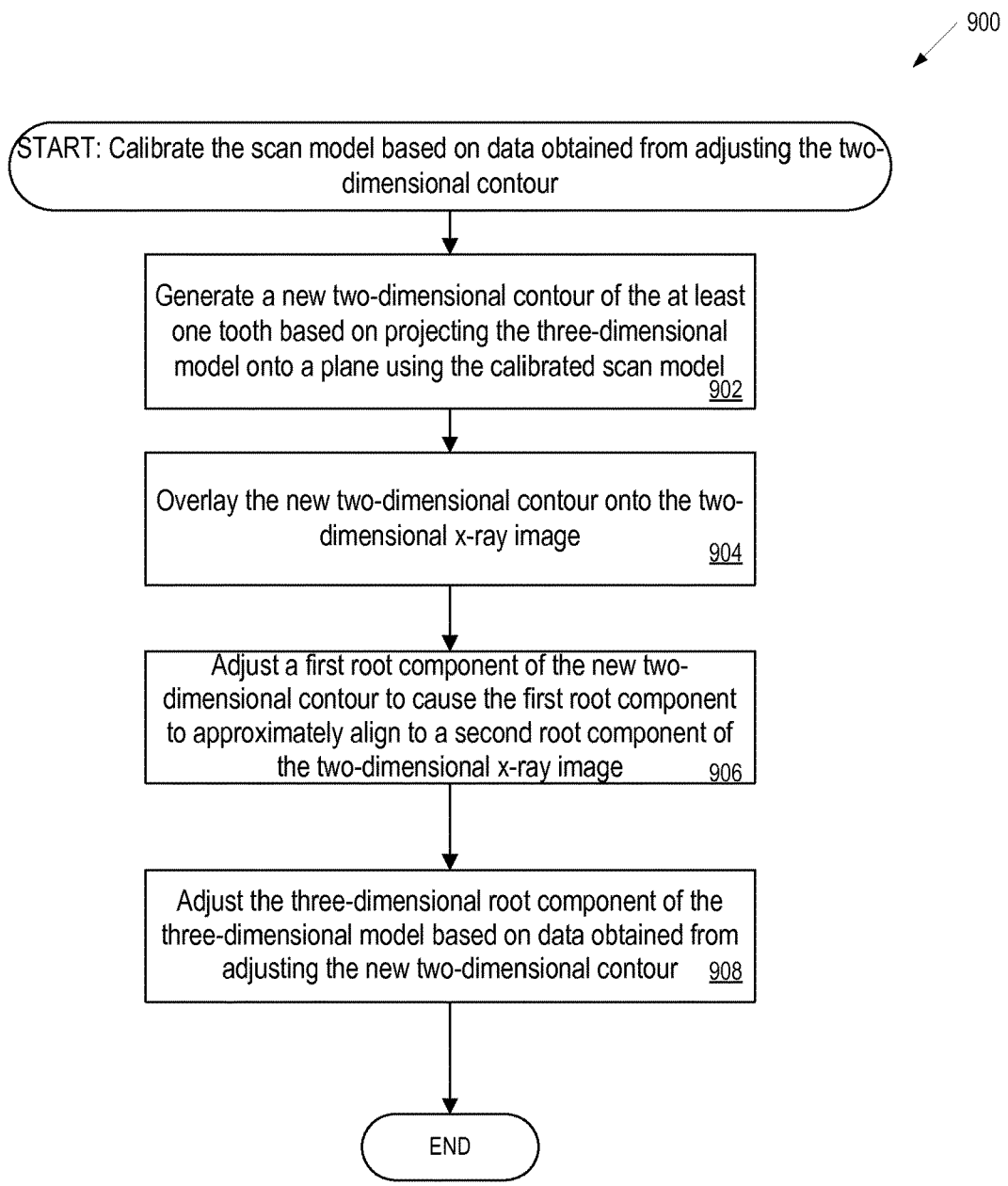
FIG. 9 illustrates a flow diagram for an exemplary method of adjusting a root component of a 2D contour after calibrating the scan model of FIG. 8, in accordance with embodiments of the present invention.

FIG. 9 illustrates a flow diagram for an exemplary method 900 of adjusting a root component of a 2D contour after calibrating the scan model of FIG. 8, in accordance with embodiments of the present invention. Method 900 may be performed by processing logic that may comprise hardware (e.g., circuitry, dedicated logic, programmable logic, microcode, etc.), software (such as instructions run on a processing device), firmware, or a combination thereof. In one implementation, method 900 may be performed by computer device 114 of FIG. 1. In another implementation, method 900 may be performed or caused to be performed all or in part by 3D model application 108 or scan model module 130 of FIG. 1. For simplicity of explanation, method 900 is depicted and described as a series of acts. However, acts in accordance with this disclosure can occur in various orders, concurrently, and/or with other acts not presented or described herein. Furthermore, not all illustrated acts may be required to implement method 900 in accordance with the disclosed subject matter. In addition, those skilled in the art will understand and appreciate that method 900 may alternatively be represented as a series of interrelated states via a state diagram or interrelated events.

Method 900 begins at block 902 after calibrating the scan model based on data obtained from adjusting the 2D contour. At block 902 processing logic performing the method generates a new 2D contour (e.g., 2D contour 402) of at least one tooth based on projecting a 3D model of one or more teeth onto a plane using the calibrated scan model. Additional details of generating a new 2D contour may be discussed with reference to FIGS. 1 and 4A. Method 900 continues to block 904, where processing logic may overlay the new 2D contour (e.g., 2D contour 402) onto the 2D x-ray image (e.g., 2D x-ray image 406). Additional details of overlaying the new 2D contour may be discussed with reference to FIGS. 1 and 4A.

Method 900 continues to block 906, where processing logic adjusts a first root component (e.g., root component 408) of the new 2D contour (e.g., 2D contour 402) to cause the root component to approximately align with a corresponding root component of the 2D x-ray image (e.g., 2D x-ray image 406). A tooth may have multiple root components, and each root component may be adjusted to align with a corresponding root component of the 2D x-ray image. In one embodiment, the first root component of the new 2D contour includes a root axis (e.g., root axis 412) and root apex (e.g., root apex 410). Adjusting the root component may include repositioning the root axis and root apex to approximately align with the corresponding root axis and root apex of the 2D x-ray image. Additional details of overlaying the new 2D contour may be discussed with reference to FIGS. 1 and 4A-C.

Method 900 continues to block 908, where processing logic may adjust the 3D root component (e.g., 3D root component 508) of the 3D model (e.g., 3D tooth model) based on data obtained from adjusting the new 2D contour (e.g., 2D contour 402). Additional details of adjusting the 3D root component may be discussed with reference to FIGS. 1 and 5A-B.

Figure 10:
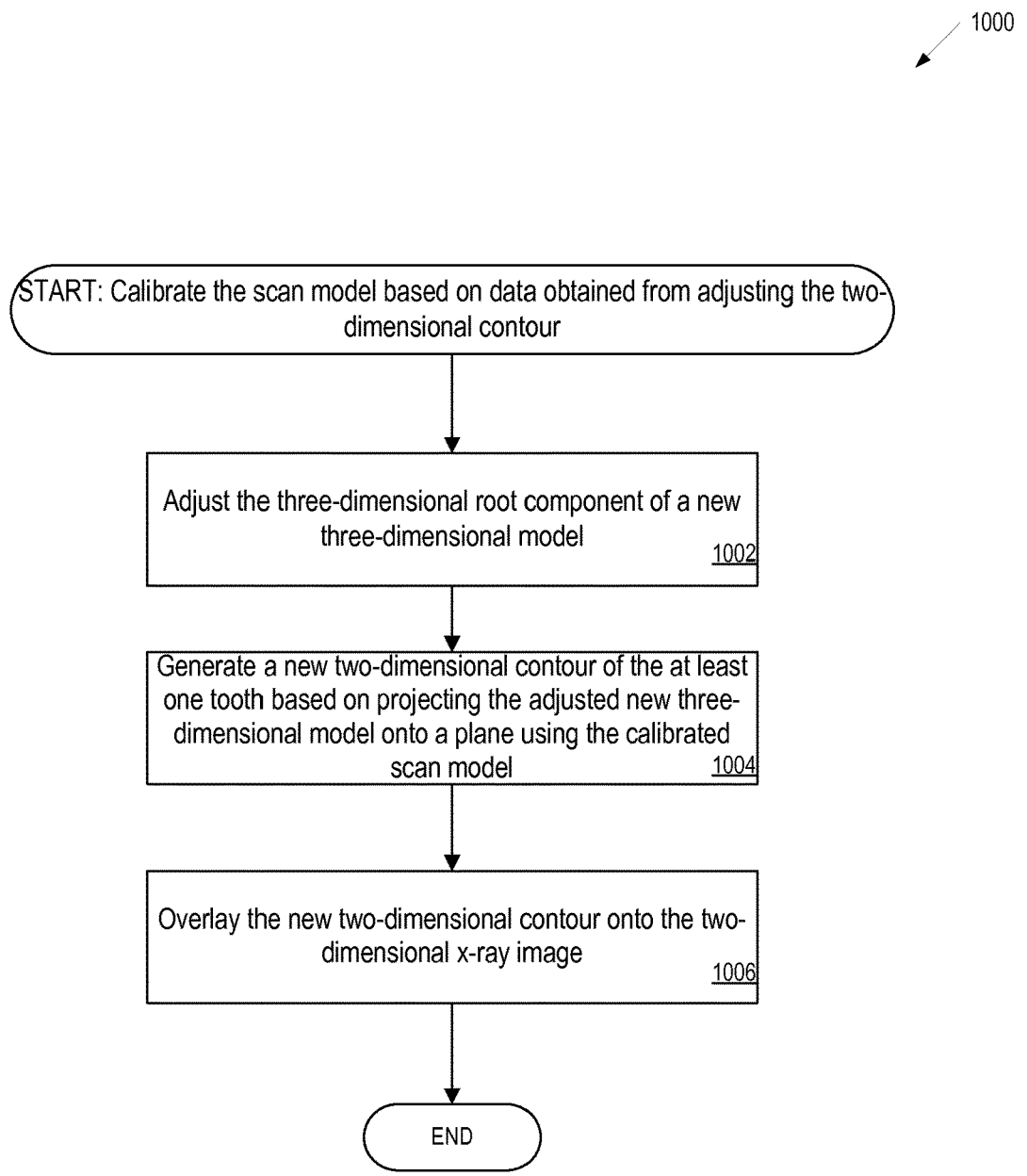
FIG. 10 illustrates a flow diagram for another exemplary method of adjusting a three-dimensional tooth model after calibrating the scan model of FIG. 8, in accordance with embodiments of the present invention.

FIG. 10 illustrates a flow diagram for another exemplary method 1000 of adjusting a three-dimensional tooth model after calibrating the scan model of FIG. 8, in accordance with embodiments of the present invention. Method 1000 may be performed by processing logic that may comprise hardware (e.g., circuitry, dedicated logic, programmable logic, microcode, etc.), software (such as instructions run on a processing device), firmware, or a combination thereof. In one implementation, method 1000 may be performed by computer device 114 of FIG. 1. In another implementation, method 1000 may be performed or caused to be performed all or in part by 3D model application 108 or scan model module 130 of FIG. 1. For simplicity of explanation, method 1000 is depicted and described as a series of acts. However, acts in accordance with this disclosure can occur in various orders, concurrently, and/or with other acts not presented or described herein. Furthermore, not all illustrated acts may be required to implement method 1000 in accordance with the disclosed subject matter. In addition, those skilled in the art will understand and appreciate that method 1000 may alternatively be represented as a series of interrelated states via a state diagram or interrelated events.

Method 1000 begins after calibrating the scan model based on data obtained from adjusting the 2D contour (e.g., 2D contour 116). Method 1000 begins at block 1002, where processing logic performing the method may adjust the 3D root component of a new 3D model. Method 1000 continues to block 1004, where processing logic may generate a new 2D contour of at least one tooth based on projecting the adjusted new 3D model onto a plane using the calibrated scan model. Method 1000 continues to block 1006 where processing logic may overlay the new 2D contour onto the 2D x-ray image (e.g., 2D x-ray image 112). Additional details of method 1000 may be discussed in reference to FIG. 4A.

Figure 11:
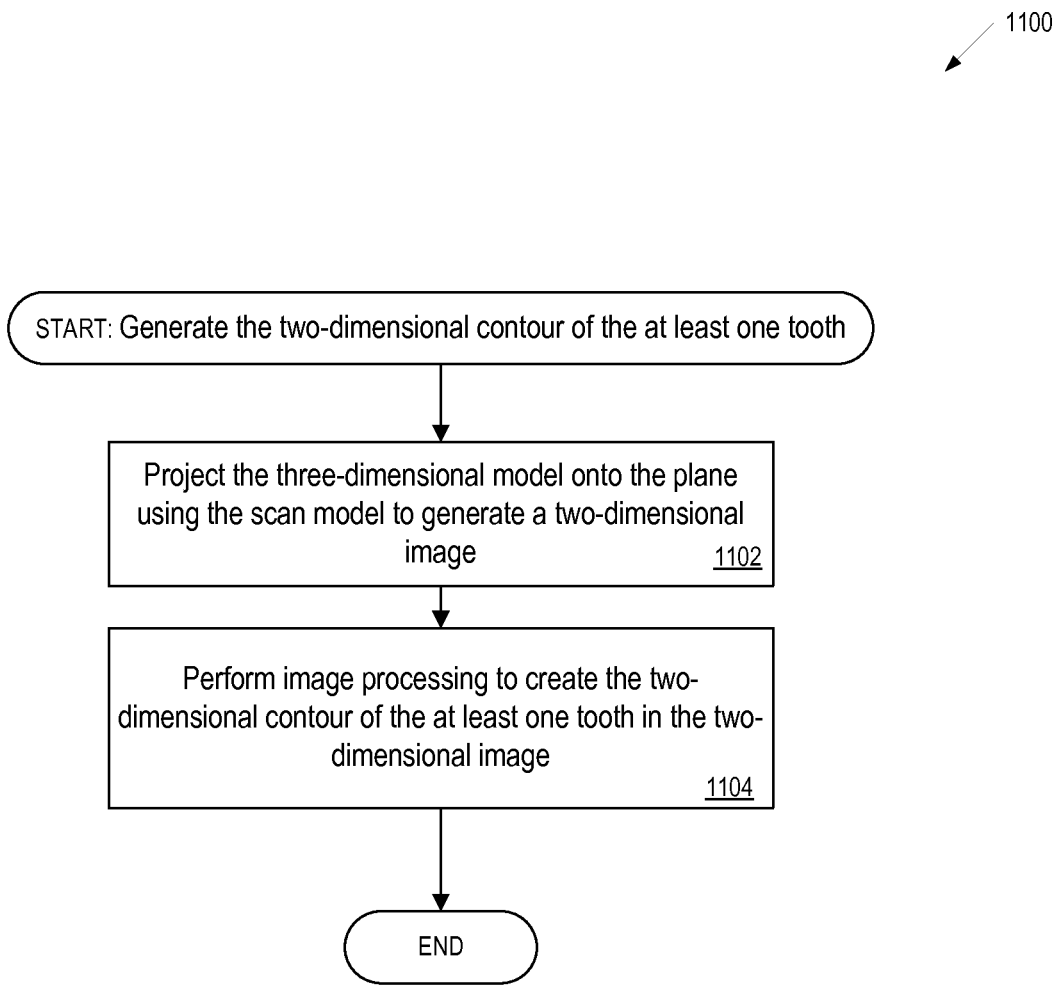
FIG. 11 illustrates a flow diagram for another exemplary method of generating a two-dimensional contour, in accordance with embodiments of the present invention.

FIG. 11 illustrates a flow diagram for another exemplary method 1100 of generating a two-dimensional contour, in accordance with embodiments of the present invention. Method 1100 may be performed by processing logic that may comprise hardware (e.g., circuitry, dedicated logic, programmable logic, microcode, etc.), software (such as instructions run on a processing device), firmware, or a combination thereof. In one implementation, method 1100 may be performed by computer device 114 of FIG. 1. In another implementation, method 1100 may be performed or caused to be performed all or in part by 3D model application 108 or scan model module 130 of FIG. 1. For simplicity of explanation, method 1100 is depicted and described as a series of acts. However, acts in accordance with this disclosure can occur in various orders, concurrently, and/or with other acts not presented or described herein. Furthermore, not all illustrated acts may be required to implement method 1100 in accordance with the disclosed subject matter. In addition, those skilled in the art will understand and appreciate that method 1100 may alternatively be represented as a series of interrelated states via a state diagram or interrelated events.

Method 1100 begins at block 1102, where processing logic performing the method may project the 3D model (e.g., initial 3D model 106) onto a plane using the scan model to generate a 2D image. Method 1100 continues to block 1104, where processing logic may perform image processing to create the 2D contour (e.g., 2D contour 116) of at least one tooth in the in the 2D image.

Figure 12:
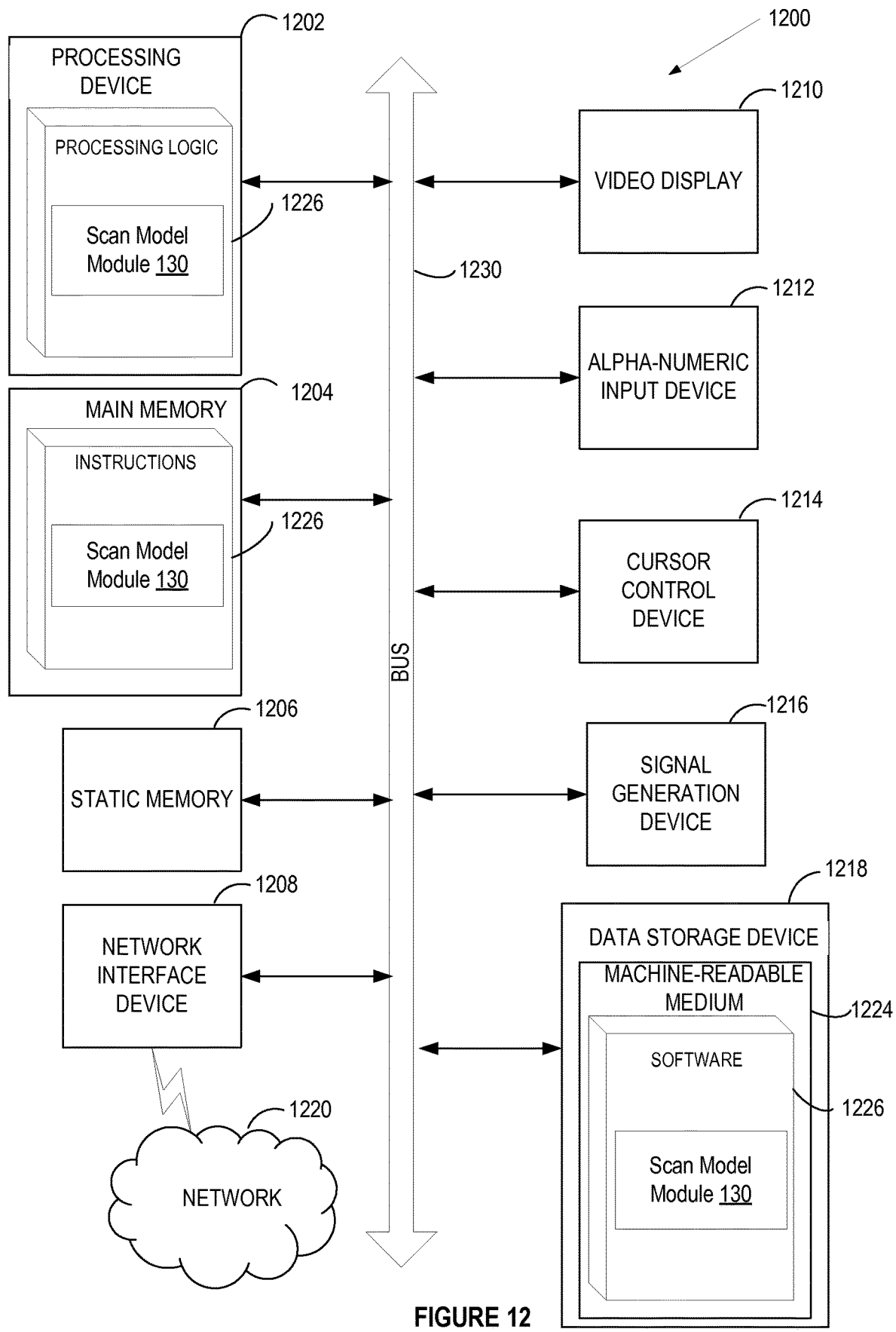
FIG. 12 illustrates a block diagram of an example computing device, in accordance with embodiments of the present invention.

FIG. 12 illustrates a block diagram of an example computing device, in accordance with embodiments of the present invention. In alternative implementations, the machine may be connected (e.g., networked) to other machines in a LAN, an intranet, an extranet, or the Internet. The machine may operate in the capacity of a server or a client device in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1200 includes a processing device 1202, a main memory 1204 (e.g., read-only memory (ROM), flash memory, dynamic random access memory (DRAM) (such as synchronous DRAM (SDRAM) or DRAM (RDRAM), etc.), a static memory 1206 (e.g., flash memory, static random access memory (SRAM), etc.), and a data storage device 1218, which communicate with each other via a bus 1230.

Processing device 1202 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 may be configured to execute the processing logic 1226 for performing the operations and steps discussed herein.

The computer system 1200 may further include a network interface device 1208 communicably coupled to a network 1220. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), and a signal generation device 1216 (e.g., a speaker).

The data storage device 1218 may include a machine-accessible storage medium 1224 on which may be stored software 1226 embodying any one or more of the methodologies of functions described herein. The software 1226 may also reside, completely or at least partially, within the main memory 1204 as instructions 1226 and/or within the processing device 1202 as processing logic 1226 during execution thereof by the computer system 1200; the main memory 1204 and the processing device 1202 also constituting machine-accessible storage media.

The machine-readable storage medium 1224 may also be used to store instructions 1226 to implement the 3D model application 108 and/or scan model module 130 to implement any one or more of the methodologies of functions described herein in a computer system, such as the system described with respect to FIG. 1, and/or a software library containing methods that call the above applications.

While the machine-accessible storage medium 1224 is shown in an example implementation to be a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that may be capable of storing, encoding or carrying a set of instruction for execution by the machine and that cause the machine to perform any one or more of the methodologies of the disclosure. The term "machine-accessible storage medium" shall accordingly be taken to include, but not be limited to, solid-state memories, and optical and magnetic media.

In the foregoing description, numerous details are set forth. It may be apparent, however, that the disclosure may be practiced without these specific details. In some instances, well-known structures and devices are shown in block diagram form, rather than in detail, in order to avoid obscuring the disclosure.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "generating", "overlaying", "adjusting", "calibrating", "detecting", "scaling", "repositioning", "projecting", "performing", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may comprise a general purpose computer selectively activated or reconfigured by a computer program stored in the computer. Such a computer program may be stored in a machine readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems may appear as set forth in the description below. In addition, the disclosure is not described with reference to any particular programming language. It may be appreciated that a variety of programming languages may be used to implement the teachings of the disclosure as described herein.

The disclosure may be provided as a computer program product, or software, that may include a machine-readable medium having stored thereon instructions, which may be used to program a computer system (or other electronic devices) to perform a process according to the disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), etc.

Whereas many alterations and modifications of the disclosure may no doubt become apparent to a person of ordinary skill in the art after having read the foregoing description, it is to be understood that any particular example shown and described by way of illustration is in no way intended to be considered limiting. Therefore, references to details of various examples are not intended to limit the scope of the claims, which in themselves recite only those features regarded as the disclosure.

What is claimed is:

1. A method comprising:
    generating, by a processing device, a scan model that is a mathematical model to simulate an imaging process performed by an x-ray imaging device that created a two-dimensional x-ray image of at least one tooth, wherein the scan model uses an initial estimate of one or more parameters of the x-ray imaging device to simulate the imaging process on a three-dimensional model of the at least one tooth to generate a two-dimensional contour of the three-dimensional model, wherein the one or more parameters comprise a scan angle parameter indicative of a scan angle of the x-ray imaging device;
    generating, by the processing device, the two-dimensional contour of the three-dimensional model based on the scan model that uses the initial estimate of the one or more parameters of the x-ray imaging device;
    adjusting the two-dimensional contour to cause a first component of the two-dimensional contour to approximately align with a second component of the two-dimensional x-ray image; and
    calibrating the scan model based on data obtained from adjusting the two-dimensional contour.

2. The method of claim 1, further comprising performing the following after calibrating the scan model:
    generating, by the processing device, a new two-dimensional contour of the at least one tooth based on projecting the three-dimensional model onto a plane using the calibrated scan model;
    overlaying the new two-dimensional contour onto the two-dimensional x-ray image, wherein a new first component of the new two-dimensional contour approximately aligns with the second component of the two-dimensional x-ray image;
    adjusting a first root component of the new two-dimensional contour to cause the first root component to approximately align to a second root component of the two-dimensional x-ray image; and
    adjusting a three-dimensional root component of the three-dimensional model based on data obtained from adjusting the new two-dimensional contour.

3. The method of claim 2, wherein the first root component of the new two-dimensional contour comprises a first root axis and a first root apex, and wherein adjusting the first root component comprises repositioning at least one of the first root axis or the first root apex to approximately align the first root axis to a second root axis of the two-dimensional x-ray image or to approximately align the first root apex to a second root apex of the two-dimensional x-ray image.

4. The method of claim 1, wherein the at least one tooth comprises a dental arch comprising a plurality of teeth, wherein the two-dimensional x-ray image comprises a panoramic x-ray image of the dental arch taken by the x-ray imaging device, wherein the scan model comprises a panoramic scan model, and wherein the two-dimensional contour of the at least one tooth comprises a distinct two-dimensional contour of each of the plurality of teeth.

5. The method of claim 4, further comprising:
adjusting at least two of the distinct two-dimensional contours; and
calibrating the scan model based on data obtained from adjusting the at least two of the distinct two-dimensional contours.

6. The method of claim 1, wherein the first component comprises a first crown component and the second component comprises a second crown component, the method further comprising:
detecting one or more feature points on a three-dimensional crown component of the three-dimensional model, wherein the first crown component of the two-dimensional contour comprises the one or more feature points, and wherein adjusting the two-dimensional contour comprises at least one of scaling the two-dimensional contour or repositioning the two-dimensional contour to approximately align the one or more feature points of the first crown component of the two-dimensional contour to one or more corresponding feature points of the second crown component of the two-dimensional x-ray image.

7. The method of claim 1, wherein calibrating the scan model comprises:
adjusting at least one of a coordinate system parameter, the scan angle parameter, an arch length parameter, or an elliptical arch parameter of the x-ray imaging device.

8. The method of claim 1, further comprising:
generating the three-dimensional model based on merging a three-dimensional crown component from a scan with a three-dimensional root component from a template;
wherein generating the two-dimensional contour of the at least one tooth comprises:
projecting the three-dimensional model onto a plane using the scan model to generate a two-dimensional image; and
subsequently performing image processing to create the two-dimensional contour of the at least one tooth in the two-dimensional image.

9. The method of claim 1, further comprising performing the following after calibrating the scan model:
adjusting a three-dimensional root component of a new three-dimensional model;
generating a new two-dimensional contour of the at least one tooth based on projecting the adjusted new three-dimensional model onto a plane using the calibrated scan model; and
overlaying the new two-dimensional contour onto the two-dimensional x-ray image, wherein a new first component of the new two-dimensional contour approximately aligns to the second component of the two-dimensional x-ray image, and wherein a first root component of the new two-dimensional contour approximately aligns to a second root component of the two-dimensional x-ray image.

10. A non-transitory computer readable storage medium comprising instructions that, responsive to being executed by a processing device, cause the processing device to perform operations comprising:
generating, by the processing device, a scan model that is a mathematical model to simulate an imaging process performed by an x-ray imaging device that created a two-dimensional x-ray image of at least one tooth, wherein the scan model uses an initial estimate of one or more parameters of the x-ray imaging device to simulate the imaging process on a three-dimensional model of the at least one tooth to generate a two-dimensional contour of the three-dimensional model, wherein the one or more parameters comprise a scan angle parameter indicative of a scan angle of the x-ray imaging device;
generating, by the processing device, the two-dimensional contour of the three-dimensional model based on the scan model that uses the initial estimate of the one or more parameters of the x-ray imaging device;
adjusting the two-dimensional contour to cause a first component of the two-dimensional contour to approximately align with a second component of the two-dimensional x-ray image; and
calibrating the scan model based on data obtained from adjusting the two-dimensional contour.

11. The non-transitory computer readable medium of claim 10, the operations further comprising performing the following after calibrating the scan model:
generating, by the processing device, a new two-dimensional contour of the at least one tooth based on projecting the three-dimensional model onto a plane using the calibrated scan model;
overlaying the new two-dimensional contour onto the two-dimensional x-ray image, wherein a new first component of the new two-dimensional contour approximately aligns to the second component of the two-dimensional x-ray image;
adjusting a first root component of the new two-dimensional contour to cause the first root component to approximately align to a second root component of the two-dimensional x-ray image; and
adjusting a three-dimensional root component of the three-dimensional model based on data obtained from adjusting the new two-dimensional contour.

12. The non-transitory computer readable medium of claim 10, wherein the first component comprises a first crown component and the second component comprises a second crown component, the operations further comprising:
detecting one or more feature points on a three-dimensional crown component of the three-dimensional model, wherein the first crown component of the two-dimensional contour comprises the one or more feature points, and wherein adjusting the two-dimensional contour comprises at least one of scaling the two-dimensional contour or repositioning the two-dimensional contour to approximately align the one or more feature points of the first crown component of the two-dimensional contour to one or more corresponding feature points of the second crown component of the two-dimensional x-ray image.

13. The non-transitory computer readable medium of claim 10, wherein calibrating the scan model, the operations comprising:
adjusting at least one of a coordinate system parameter, the scan angle parameter, an arch length parameter, or an elliptical arch parameter of the x-ray imaging device.

14. The non-transitory computer readable medium of claim 10, the operations further comprising:

generating the three-dimensional model based on merging a three-dimensional crown component from a scan with a three-dimensional root component from a template;

wherein generating the two-dimensional contour of the at least one tooth comprises:

projecting the three-dimensional model onto a plane using the scan model to generate a two-dimensional image; and subsequently performing image processing to create the two-dimensional contour of the at least one tooth in the two-dimensional image.

15. A system comprising:

a memory; and a processing device, coupled to the memory, the processing device to:

generate, by the processing device, a scan model that is a mathematical model to simulate an imaging process performed by an x-ray imaging device that created a two-dimensional x-ray image of at least one tooth, wherein the scan model uses an initial estimate of one or more parameters of the x-ray imaging device to simulate the imaging process on a three-dimensional model of the at least one tooth to generate a two-dimensional contour of the three-dimensional model, wherein the one or more parameters comprise a scan angle parameter indicative of a scan angle of the x-ray imaging device;

generate, by the processing device, the two-dimensional contour of the three-dimensional model based on the scan model that uses the initial estimate of the one or more parameters of the x-ray imaging device;

adjust, by the processing device, the two-dimensional contour to cause a first component of the two-dimensional contour to approximately align with a second component of the two-dimensional x-ray image; and calibrate the scan model based on data obtained from adjusting the two-dimensional contour.

16. The system of claim 15, the processing device further to perform the following after calibrating the scan model:

generate, by the processing device, a new two-dimensional contour of the at least one tooth based on projecting the three-dimensional model onto a plane using the calibrated scan model;

overlay the new two-dimensional contour onto the two-dimensional x-ray image, wherein a new first component of the new two-dimensional contour approximately aligns with the second component of the two-dimensional x-ray image;

adjust a first root component of the new two-dimensional contour to cause the first root component to approximately align to a second root component of the two-dimensional x-ray image; and adjust a three-dimensional root component of the three-dimensional model based on data obtained from adjusting the new two-dimensional contour.

17. The system of claim 15, wherein the first component comprises a first crown component and the second component comprises a second crown component, the processing device further to:

detect one or more feature points on a three-dimensional crown component of the three-dimensional model, wherein the first crown component of the two-dimensional contour comprises the one or more feature points, and wherein adjusting the two-dimensional contour comprises at least one of scaling the two-dimensional contour or repositioning the two-dimensional contour to approximately align the one or more feature points of the first crown component of the two-dimensional contour to one or more corresponding feature points of the second crown component of the two-dimensional x-ray image.

18. The system of claim 15, wherein calibrating the scan model the processing device to:

adjust at least one of a coordinate system parameter, the scan angle parameter, an arch length parameter, or an elliptical arch parameter of the x-ray imaging device.

19. The system of claim 15, the processing device further to:

generate the three-dimensional model based on merging a three-dimensional crown component from a scan with a three-dimensional root component from a template;

wherein generating the two-dimensional contour of the at least one tooth comprises:

projecting the three-dimensional model onto a plane using the scan model to generate a two-dimensional image; and subsequently performing image processing to create the two-dimensional contour of the at least one tooth in the two-dimensional image.

20. The system of claim 15, the processing device further to perform the following after calibrating the scan model:

adjust a three-dimensional root component of a new three-dimensional model;

generate a new two-dimensional contour of the at least one tooth based on projecting the adjusted new three-dimensional model onto a plane using the calibrated scan model; and overlay the new two-dimensional contour onto the two-dimensional x-ray image, wherein a new first component of the new two-dimensional contour approximately aligns to the second component of the two-dimensional x-ray image, and wherein a first root component of the new two-dimensional contour approximately aligns to a second root component of the two-dimensional x-ray image.

* * * * *